US012765791B2

(12) United States Patent
Marks et al.

(10) Patent No.: US 12,765,791 B2
(45) Date of Patent: Oct. 20, 2026

(54) CROSS-DOMAIN UNROLLING-BASED IMAGING PHOTOPLETHYSMOGRAPHY SYSTEMS AND METHODS FOR ESTIMATING VITAL SIGNS

(71) Applicant: Mitsubishi Electric Research Laboratories, Inc., Cambridge, MA (US)

(72) Inventors: Tim Marks, Newton, MA (US); Vineet Shenoy, Princeton, NJ (US); Hassan Mansour, Newton, MA (US); Suhas Lohit, Somerville, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 410 days.

(21) Appl. No.: 18/460,985

(22) Filed: Sep. 5, 2023

(65) Prior Publication Data

US 2025/0072773 A1 Mar. 6, 2025

(51) Int. Cl.
*A61B 5/024* (2006.01)
*A61B 5/00* (2006.01)

(52) U.S. Cl.
CPC ...... *A61B 5/02427* (2013.01); *A61B 5/02405* (2013.01); *A61B 5/7203* (2013.01);
(Continued)

(58) Field of Classification Search
CPC ............ A61B 2503/22; A61B 5/02405; A61B 5/02416; A61B 5/02427; A61B 5/7203;
(Continued)

(56) References Cited

U.S. PATENT DOCUMENTS 11,259,710 B2 3/2022 Merl
2020/0121256 A1* 4/2020 Mcduff .................... G06N 3/09
(Continued)

OTHER PUBLICATIONS

Nowara, Ewa M., Daniel McDuff, and Ashok Veeraraghavan. "The benefit of distraction: Denoising camera-based physiological measurements using inverse attention." In Proceedings of the IEEE/CVF International Conference on Computer Vision, pp. 4955-4964. 2021.

(Continued)

*Primary Examiner* — Shahdeep Mohammed
(74) *Attorney, Agent, or Firm* — Gene Vinokur

(57) ABSTRACT

A computer-implemented method for estimating a vital sign of a subject comprises receiving a sequence of imaging photoplethysmography (iPPG) signals measured from different regions of a skin of the subject and executing a cross-domain unrolling optimization iteratively minimizing a difference between the received iPPG signals and reconstructed iPPG signals followed by processing the reconstructed iPPG signals with an iPPG neural network trained in the frequency domain with machine learning to enforce a learned structure on the frequency coefficients of the reconstructed iPPG signals. The method further comprises determining the vital sign signal of the subject from the frequency coefficients of the reconstructed iPPG signals upon reaching a termination condition of the cross-domain unrolling optimization and outputting the vital sign signal corresponding to the reconstructed iPPG signals.

20 Claims, 14 Drawing Sheets

(52) U.S. Cl.
CPC .......... *A61B 5/7257* (2013.01); *A61B 5/7267* (2013.01); *A61B 5/7475* (2013.01); *A61B 2503/22* (2013.01)

(58) Field of Classification Search
CPC ... A61B 5/7257; A61B 5/7264; A61B 5/7267; A61B 5/7278; A61B 5/7475; G16B 20/00; G16B 20/20; G16B 20/40; G16B 30/00
See application file for complete search history.

(56) References Cited

U.S. PATENT DOCUMENTS

| | | | |
|---|---|---|---|
| 2021/0224983 | A1 | 7/2021 | Merl |
| 2023/0063221 | A1 | 3/2023 | Merl |

OTHER PUBLICATIONS

Tulyakov, Sergey, Xavier Alameda-Pineda, Elisa Ricci, Lijun Yin, Jeffrey F. Cohn, and Nicu Sebe. "Self-adaptive matrix completion for heart rate estimation from face videos under realistic conditions." In Proceedings of the IEEE conference on computer vision and pattern recognition, pp. 2396-2404. 2016.

* cited by examiner

| Heart rate estimation results on the MMSE-HR dataset | | | |
|---|---|---|---|
| ***Method*** | ***MAE (bpm)* ↓** | ***RMSE (bpm)* ↓** | ***PTE (6%)* ↑** |
| ICA | 5.44 | 12.00 | - |
| CHROM | 3.74 | 8.11 | - |
| POS | 3.90 | 9.61 | - |
| CAN | 4.06 | 9.51 | - |
| InverseCAN | 2.27 | 4.90 | - |
| AutoSparsePPG | 4.55 | 14.42 | 88.10 |
| TURNIP | 1.17 ± 0.01 | 3.46 ± 0.21 | 93.21 ± 1.14 |
| Unrolled iPPG | 1.11 ± 0.01 | 2.97 ± 0.17 | 93.53 ± 0.73 |

FIG. 4

| Heart rate estimation results with and without modelling the noise component E | | | |
|---|---|---|---|
| ***Method*** | ***MAE (bpm)*** ↓ | ***RMSE (bpm)*** ↓ | ***PTE (6%)*** ↑ |
| Without Q | 1.44 | 3.87 | 92.25 |
| With Q | 1.11 | 2.82 | 93.02 |

FIG. 6

| Heart rate estimation performance based on the number *T* of unrolling iterations | | | |
|---|---|---|---|
| ***No. of iterations*** | ***MAE (bpm)*** ↓ | ***RMSE (bpm)*** ↓ | ***PTE (6%)*** ↑ |
| 1 | 1.33 | 3.12 | 92.25 |
| 3 | 1.11 | 3.22 | 93.02 |
| 5 | 2.14 | 6.72 | 90.7 |
| 10 | 2.59 | 8.89 | 90.7 |

FIG. 7

CROSS-DOMAIN UNROLLING-BASED IMAGING PHOTOPLETHYSMOGRAPHY SYSTEMS AND METHODS FOR ESTIMATING VITAL SIGNS

TECHNICAL FIELD

The present disclosure relates generally to remotely monitoring vital signs of subjects and more particularly to imaging photoplethysmography (iPPG) systems and methods for remote measurement of vital signs.

BACKGROUND

Vital signs of a person, for example heart rate (HR), heart rate variability (HRV), respiration rate (RR), or blood oxygen saturation, serve as indicators of a person's current state and as a potential predictor of serious medical events. For this reason, vital signs are extensively monitored in inpatient and outpatient care settings, at home, and in other health, leisure, and fitness settings. One way of measuring the vital signs is plethysmography which corresponds to measurement of volume changes of an organ or a body part of a person. There are various implementations of plethysmography, such as Photoplethysmography (PPG) which is an optical measurement technique that evaluates a time-variant change of light reflectance or transmission of an area or volume of interest, which can be used to detect blood volume changes in microvascular bed of tissue. PPG is based on a principle that blood absorbs and reflects light differently than surrounding tissue, so variations in the blood volume with every heartbeat affect light transmission or reflectance correspondingly.

Conventional non-invasive instruments for measuring vital signs of a person, often need to be attached to the skin of the person, for instance to a fingertip, earlobe, or forehead. This may not be pleasant to the person for several reasons. Additionally, the sensor's incidence window may be too large or too small for some patients and as such may not provide correct readings. Furthermore, in view of outbreaks of contagious diseases such as the SARS-CoV-2 based novel coronavirus disease, the use of non-contact non-invasive techniques for measuring vital signs has become essential. Recent years have witnessed increasing interest in non-contact monitoring of vital signs using cameras, particularly for telemedicine, including estimation of heart rate, breathing rate, and blood pressure from video of the face or some other body part of a subject. The main advantage of monitoring vital signs of a person using a camera, rather than using a conventional contact sensor is easier usage. Cameras also provide vital sign information over a larger spatial region naturally, compared to having a highly localized contact sensor. Also the granularity of the output data can be fine tuned based on the resolution and capability of the camera sensors.

In addition to healthcare, remote monitoring can be used in safety-critical applications such as driving or heavy equipment operation, as there is no requirement of attaching a contact sensor to the operator's body, which can otherwise hinder normal operation of the users. Cameras recording facial videos capture the subtle changes in skin color corresponding to the blood volume pulse. However, the captured videos are also marred by noise due to several factors. For example, some vital signs such as the blood volume pulse signal component is a small fraction of the pixel intensity and can be easily masked by illumination changes and motion. Therefore, in order to perform an accurate measurement of the vital signs, it is important various types of noises are taken into consideration as a part of the vital sign estimation.

Some attempts in this direction have been made using blind source separation methods, model based methods, and data driven methods. However, these approaches have not been effective in recovering or extracting the underlying pulse signal due to several reasons. For example, the model-based methods are not effective in recovering the underlying pulse signal as the handcrafted constraints are too simple and do not account for all the characteristics of the signal. On the other hand, purely data-driven deep learning-based methods lack good interpretability of the underlying approach since they are black-box methods and offer low interpretability. Another challenge faced by conventional vital sign estimation approaches is that the domain in which the measurement happens may not be the appropriate domain where the underlying pulse wave can be recovered.

Hence there is a need for developing solutions for remote estimation of vital signs, that are effective, are based on data-driven modeling of both the pulse wave as well as the structured noise, and at the same time maintain interpretability. Furthermore, there is also a need to develop solutions that can operate on the measurements on multiple domains simultaneously to model both the pulse wave and the structured noise components in the respective appropriate domains, and recover the vital signs accurately.

SUMMARY

It is an objective of some example embodiments to provide effective solutions for estimating vital signs of a subject by remote photoplethysmography based approaches. It is also an objective of some example embodiments to provide such solutions with good interpretability of the underlying approach while providing accurate measurements of the vital signs. Some example embodiments are also directed towards the objective of providing such solutions that take into consideration all the characteristics of the measured signals when attempting to recover the underlying pulse signals from the measured signals. Some example embodiments are also directed towards the objective of recovering the underlying pulse signals in a domain different from that of the measured signals to separate out the noise, thereby providing greater accuracy in the estimation of the vital signs.

Some example embodiments are based on the realization that one way to model the pulse signal is to model it as a sparse signal in the Fourier domain and use variations of the Iterative Shrinkage Thresholding Algorithm (ISTA) to estimate this sparse signal from a noisy time series obtained from various facial regions. Some example embodiments realize that such ways of modelling the signal as sparse in the frequency domain and noise as sparse in the spatio-temporal domain are based on two assumptions: (1) that the true pulse signal can be modeled using a sparse set of frequencies that are shared across face regions; and (2) that the noise primarily affects a small number of regions. Accordingly, it is a realization of some example embodiments that in such approaches, solving for the signal and noise components may be done via alternating gradient updates and soft-thresholding projection.

Some example embodiments realize that remote estimation of signs such as the pulse wave and heart rate from videos, known as imaging photoplethysmography (iPPG) or remote photoplethysmography (rPPG), can be categorized into blind source separation methods, model-based methods, and data-driven methods. Blind source separation assumes that the extracted time-series signal is composed of both the noise and the underlying pulse signal, and that these signals are either statistically independent or uncorrelated. Techniques such as Independent Component Analysis (ICA) and Principal Components Analysis (PCA) separate the signal from the noise. Some example embodiments also realize that another approach to this task is to explicitly model light absorption and reflection in the skin; both aiming to reduce the dependence of the extracted signal on the average skin reflection color. Some example embodiments realize that the model based methods model the underlying pulse waveform as the sum of a sparse set of periodic signals, and they aim to solve for the underlying pulse waveform. Some example embodiments are also based on the realization that another approach to the task of recovering the underlying pulse signal may be based on data-driven methods which learn directly from the training data and are typically instantiated as neural networks, whose parameters are learned by minimizing a loss between the output of the network and the ground-truth waveform.

Some example embodiments are based on another realization that unrolling optimization algorithms integrate learnable parameters into traditional iterative algorithms, harnessing the power of learning while exploiting known structures and retaining interpretability. These algorithms repeatedly apply two steps: first, they ensure that the intended result is consistent with measurements by minimizing a data fidelity term using a learned or fixed forward operator, and second, they apply a signal denoiser using a learned signal prior to fit the solution to a ground-truth signal.

Based on several experiments, it is a realization of some example embodiments that currently, the signal denoiser of the second step is applied to the data in the original domain of the measurements. This should not come as a surprise because the objective of the denoiser is to remove the noise caused by the imperfections of the measurements made in the original measurement domain. However, some embodiments are based on the recognition that for some applications it is beneficial to apply the signal denoiser in a domain different from the measurement domain. For example, for some applications, the data in that different domain can have a better structure or salient structure suitable for machine learning, and/or the ground truth data can be measured in that different domain, etc.

Such a cross-domain unrolling optimization is non-conventional because conventionally, the denoiser should act on the noise caused by the noisy measurements. However, some embodiments are based on a realization that when the denoiser is applied in a domain different from the original domain of the measurements, the denoiser acts as a structure enforcer and/or a structure prior. This understanding reinforces the selection of the domain that has the salient structure. Additionally or alternatively, this understanding means that the noise can be constructed separately in a manner similar to constructing the signal of interest.

Some embodiments are based on the realization that contactless vital sign estimation can benefit from this cross-domain unrolling optimization. To that end, it is an object of some embodiments to adapt an unrolling optimization algorithm for imaging photoplethysmography (iPPG), to estimate a subject's vital signals such as pulse signal, heart rate, and/or other vital signs from video. Additionally or alternatively, it is an object of some embodiments to disclose an unrolled iPPG method that integrates iterative optimization updates with deep learning-based signal priors to estimate the pulse waveform and heart rate from facial videos.

Some embodiments are based on an understanding that the two steps of the unrolling algorithm are typically performed in the same domain. For example, for image processing applications both steps of the unrolling algorithm are performed in the feature domain of the images. In theory, this approach can be extended to the time-series noisy measurements of iPPG by performing signal denoising in the time domain. This would make sense because the noise of the noisy measurements comes from that domain.

However, after some experiments, some embodiments realized the benefits of applying the signal denoiser of the second step directly in the frequency domain, in order to extract the pulse signal of interest. This is advantageous because the denoiser can be trained with ground-truth data of the pulse signal, which is measured in a contact manner. In addition, in the frequency domain, the pulse signal has a more consistent structure than in the time domain. In effect, the signal denoiser acts as a structure prior. One consequence is that the noise can be optionally modeled separately with another noise estimator that has been trained to determine the structure of the noise.

Towards these ends, it is an objective of some example embodiments to provide systems, methods and computer program products that effectively estimate vital signs of a subject using a cross-domain unrolling optimization approach. The disclosed embodiments model the signal extracted from video of a subject as the sum of an underlying pulse signal and noise. However, instead of explicitly imposing a handcrafted prior (e.g., sparsity in the frequency domain) on the signal, some example embodiments learn priors on the signal and noise using neural networks. Some of the disclosed embodiments solve for the underlying pulse signal by unrolling proximal gradient descent, wherein the algorithm alternates between gradient descent steps and application of learned denoisers, which replace handcrafted priors and their proximal operators. In other words, some embodiments combine a model-based approach with a data-driven deep neural network for estimation of the vital signs. Using this approach, some of the disclosed embodiments achieve accurate estimation of the vital signs of the subject using the challenging MMSE-HR dataset.

The models utilized by various example embodiments consider all the variations in real-world data by utilizing trainable parameters in the form of deep denoisers that can better model the signal and noise characteristics using training data, thereby leading to improved estimation of the vital signs. Some example embodiments also provide better interpretability in terms of what the model is doing to estimate the vital signs, for example by visualizing the intermediate gradient descent steps and the denoiser outputs. Thus, the disclosed embodiments provide a hybrid approach that unrolls the iterations of a model-based method and replaces any handcrafted model with deep denoisers that are trainable using training data.

In order to achieve the aforesaid objectives and advancements, some example embodiments provide systems, methods, and computer program products for estimating a vital sign signal of a subject.

Some example embodiments provide a remote photoplethysmography (RPPG) system for estimating the vital sign signal of the subject. The system comprises memory configured to store instructions and a processor configured to execute the instructions to cause the RPPG system to receive a sequence of imaging photoplethysmography (iPPG) signals measured from different regions of a skin of the subject in a time domain. The processor is also configured to execute a cross-domain unrolling optimization iteratively minimizing a difference between the received iPPG signals and reconstructed iPPG signals followed by processing the reconstructed iPPG signals with an iPPG neural network. The reconstructed iPPG signals have frequency coefficients determined in a frequency domain and transformed into the time domain of the received iPPG signals. The iPPG neural network is trained in the frequency domain with machine learning to enforce a learned structure on the frequency coefficients of the reconstructed iPPG signals. The processor is further configured to determine the vital sign signal of the subject from the frequency coefficients of the reconstructed iPPG signals upon reaching a termination condition of the cross-domain unrolling optimization and output the vital sign signal corresponding to the reconstructed iPPG signals via an output interface.

In yet another example embodiments, a computer-implemented method for estimating the vital sign of the subject is provided. The method comprises receiving a sequence of imaging photoplethysmography (iPPG) signals measured from different regions of a skin of the subject in a time domain and executing a cross-domain unrolling optimization iteratively minimizing a difference between the received iPPG signals and reconstructed iPPG signals followed by processing the reconstructed iPPG signals with an iPPG neural network. The reconstructed iPPG signals have frequency coefficients determined in a frequency domain and transformed into the time domain of the received iPPG signals. The iPPG neural network is trained in the frequency domain with machine learning to enforce a learned structure on the frequency coefficients of the reconstructed iPPG signals. The method further comprises determining the vital sign signal of the subject from the frequency coefficients of the reconstructed iPPG signals upon reaching a termination condition of the cross-domain unrolling optimization and outputting the vital sign signal corresponding to the reconstructed iPPG signals via an output interface.

In yet some other example embodiments, a non-transitory computer readable medium having stored thereon computer executable instructions for performing a method for estimating the vital sign of the subject is provided. The method comprises receiving a sequence of imaging photoplethysmography (iPPG) signals measured from different regions of a skin of the subject in a time domain and executing a cross-domain unrolling optimization iteratively minimizing a difference between the received iPPG signals and reconstructed iPPG signals followed by processing the reconstructed iPPG signals with an iPPG neural network. The reconstructed iPPG signals have frequency coefficients determined in a frequency domain and transformed into the time domain of the received iPPG signals. The iPPG neural network is trained in the frequency domain with machine learning to enforce a learned structure on the frequency coefficients of the reconstructed iPPG signals. The method further comprises determining the vital sign signal of the subject from the frequency coefficients of the reconstructed iPPG signals upon reaching a termination condition of the cross-domain unrolling optimization and outputting the vital sign signal corresponding to the reconstructed iPPG signals via an output interface.

In some example embodiments, the cross-domain unrolling optimization estimates noise of the received iPPG signals and modifies the reconstructed iPPG signals with the estimated noise for minimizing the difference between the received iPPG signals and the reconstructed iPPG signals. The noise may be processed with a noise neural network to enforce an implicit structure on the noise and generate a structured component of the noise.

In some example embodiments, the received iPPG signals are estimated in the frequency domain and the noise neural network processes the noise in the frequency domain to constrain the received iPPG signals to be limited to a set of active frequency coefficients. The received iPPG signals may be transformed into the time domain before combining with the reconstructed iPPG signals in the time domain.

In some example embodiments, the noise is estimated in the time domain, and the noise neural network may process the noise in the time domain to constrain the structure of the noise in a manner defined by the noise neural network.

BRIEF DESCRIPTION OF THE DRAWINGS

The presently disclosed embodiments will be further explained with reference to the following drawings. The drawings shown are not necessarily to scale, with emphasis instead generally being placed upon illustrating the principles of the presently disclosed embodiments.

FIG. 4 illustrates a tabular comparison of performance of the unrolled iPPG system of FIG. 1A with that of some known methods;

FIG. 6 shows the effect of explicitly modeling the structured noise component with a separate denoiser on heart rate estimation performance, according to some example embodiments;

FIG. 7 shows the effect of the number of unrolling iterations on the heart rate estimation performance, according to some example embodiments;

Figure 1A:
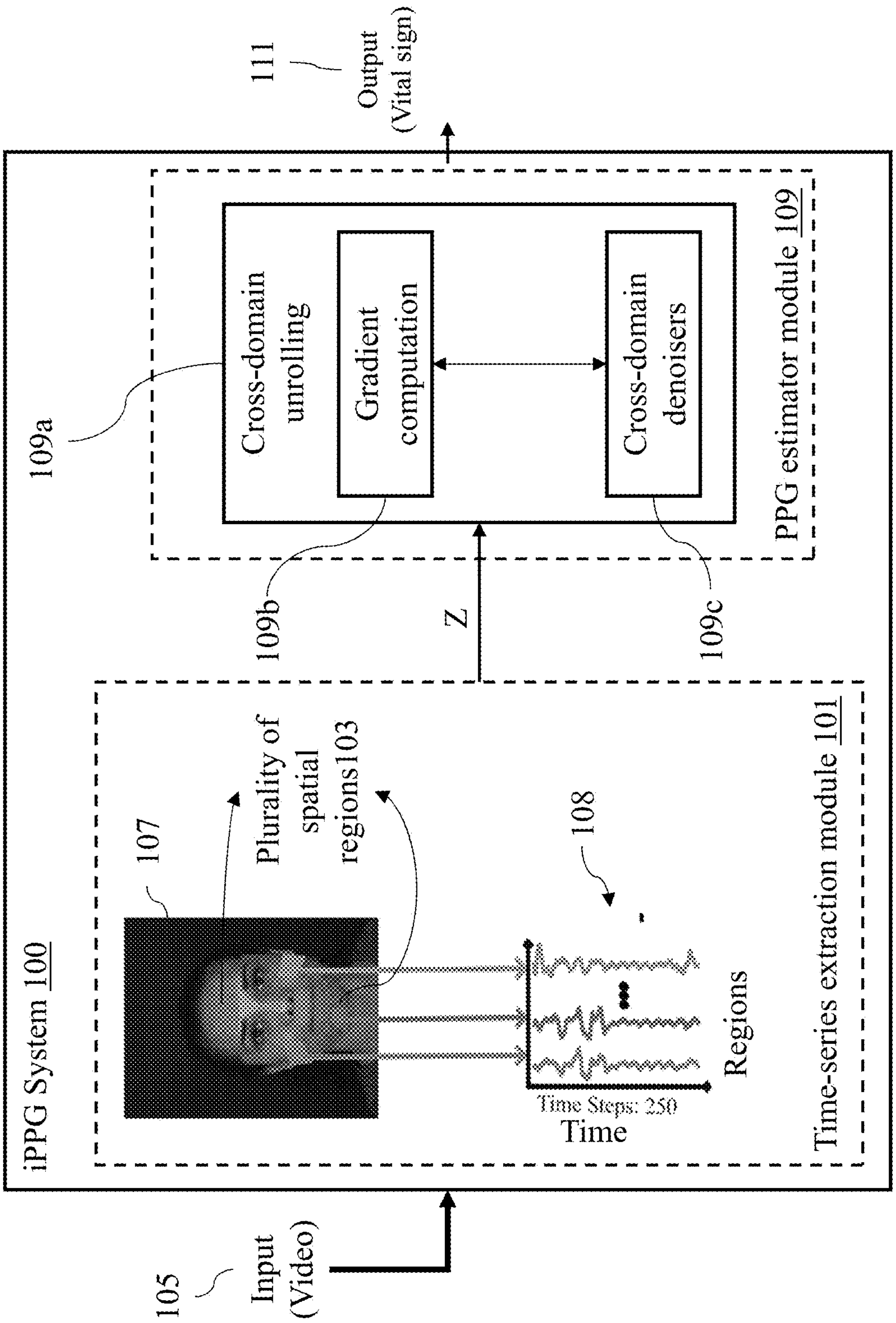
FIG. 1A illustrates a block diagram of an imaging photoplethysmography (iPPG) system for estimating a vital sign of a subject, according to some example embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. Contemplated are various changes that may be made in the function and arrangement of elements without departing from the spirit and scope of the subject matter disclosed as set forth in the appended claims.

Specific details are given in the following description to provide a thorough understanding of the embodiments. However, understood by one of ordinary skill in the art can be that the embodiments may be practiced without these specific details. For example, systems, processes, and other elements in the subject matter disclosed may be shown as components in block diagram form in order not to obscure the embodiments in unnecessary detail. In other instances, well-known processes, structures, and techniques may be shown without unnecessary detail in order to avoid obscuring the embodiments. Further, like-reference numbers and designations in the various drawings may indicate like elements.

Also, individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed but may have additional steps not discussed or included in a figure. Furthermore, not all operations in any particularly described process may occur in all embodiments. A process may correspond to a method, a function, a procedure, a subroutine, a subprogram, etc. When a process corresponds to a function, the function's termination can correspond to a return of the function to the calling function or the main function.

Furthermore, embodiments of the subject matter disclosed may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine-readable medium. A processor(s) may perform the necessary tasks.

Recently, non-contact, remote PPG (RPPG) devices for unobtrusive measurements have been introduced. RPPG utilizes light sources or, in general, radiation sources disposed remotely from a subject of interest. Similarly, a detector, e.g., a camera or a photo detector, can be disposed remotely from the person of interest. Therefore, remote photoplethysmography systems and devices are considered unobtrusive and well suited for medical as well as non-medical everyday applications. One of the advantages of camera-based vital signs monitoring versus on-body sensors is the high ease-of-use: there is no need to attach a sensor; just aiming the camera at the person is sufficient. Another advantage of camera-based vital signs monitoring over on-body sensors is the potential for achieving motion robustness: cameras have greater spatial resolution than contact sensors, which mostly include a single-element detector. RPPG technology faces a major challenge when it comes to providing accurate measurements under motion/light distortions. Particularly, the pulse signal that contains information from the subject's body is engulfed with noise that gets into the measurement due to several reasons. As such, the vital sign component is only a small fraction of the pixel intensity and can be easily masked by illumination changes and motion. Therefore, in order to perform an accurate measurement of the vital signs, it is important various types of noises are taken into consideration as a part of the vital sign estimation.

Example embodiments disclosed herein provide solutions for remote estimation of vital signs, that are effective, are based on data-driven modeling of both the pulse wave as well as the structured noise, and at the same time maintain interpretability. Some example embodiments also provide capabilities to operate on the measurements on multiple domains simultaneously to model both the pulse wave and the structured noise components in the respective appropriate domains, and recover the vital signs accurately. Some example embodiments are also directed towards the objective of recovering the underlying pulse signals in a domain different from that of the measured signals to separate out the noise, thereby providing greater accuracy in the estimation of the vital signs.

FIG. 1A illustrates a block diagram of an imaging photoplethysmography (iPPG) system 100 for estimating a vital sign of a subject, according to some example embodiments. The subject may be a human or an animal. The iPPG system 100 comprises a time-series extraction module 101 and a PPG estimator module 109 for generating a PPG waveform (also referred to as "PPG signal") given a video of different regions of skin of the subject as an input. The generated PPG waveform may be further processed to estimate some vital signs of the subject. Each of the time-series extraction module 101 and the PPG estimator module 109 may be embodied as a combination of hardware and software.

In some embodiments, the iPPG system 100 may optionally include an illumination source of visible wavelengths, near infrared (NIR) wavelengths or a broad spectrum with visible and NIR wavelengths. The illumination source may be configured to illuminate the skin of the subject. The iPPG system 100 may also optionally comprise a camera configured to capture a video 105 in the respective wavelengths of at least one body part of the subject (such as the face of the subject). In some example embodiments, the imaging setup comprising the illumination source and the camera may be external to the iPPG system 100. Irrespective of whether the imaging setup is part of the iPPG system 100 or not, the iPPG system 100 receives the captured video 105 of the subject as an input. The captured video 105 may correspond to the face of the subject. The video 105 includes a plurality of frames such that the video 105 contains an image of the face of the subject in each of the frames. One example of the image of the face of the subject as captured in at least one of the frames of the video 105 is shown as the image 107.

In some example embodiments, the time series extraction module 101 may partition the image 107 in each frame of the video 105 into a plurality of spatial regions 103, where the plurality of spatial regions 103 is analyzed jointly to accurately determine the PPG waveform. The partitioning (segmentation) of each image 107 is based on the realization that specific areas of the body part under consideration contain the strongest PPG signal. For example, specific areas of a face (also referred to as "regions of interest (ROIs)") containing the strongest PPG signals are areas located around forehead, cheeks, and chin (as shown in FIG. 1A). The partitioning of each image 107 results into a sequence of images comprising different spatial regions of the plurality of spatial regions 103, where each spatial region comprises data corresponding to at least one body part such as the skin of the subject. Further, each spatial region of the plurality of spatial regions 103 may be used to determine a PPG signal.

The sensitivity of PPG signals to noise in measurements of intensities (e.g., pixel intensities in images) of a skin of a subject is caused at least in part by independent estimation of PPG signals from the intensities of a skin of the subject measured at different spatial positions (or spatial regions). At different locations, e.g., at different regions of the skin of the subject, the measurement intensities may be subjected to different measurement noise. When the PPG signals are independently estimated from intensities at each spatial region (e.g., the PPG signal estimated from intensities at one skin region is estimated independently of the intensities or estimated signals from other skin regions), the independence of the different estimates may cause an estimator to fail to identify such noise affecting accuracy in determining the PPG signal.

The noise includes one or more of illumination variations, pixel blurs due to motion of the person, and the like. Also, vital signs such as heartbeat is a common source of the intensity variations present in the different regions of the skin. Thus, the effect of the noise on the quality of the vital signs' estimation may be reduced when the independent estimation is replaced by a joint estimation of PPG signals measured from the intensities at different regions of the skin of the subject.

For example, within the context of performing vital sign estimation using video of face of a subject, it may be contemplated that some facial regions are physiologically known to contain better PPG signals. However, the "goodness" of these facial regions also depends on several factors such as the particular conditions in which the video was captured, facial hair of the subject, or facial occlusions and the like. Therefore, it is beneficial to identify which regions are likely to contain the most noise and remove them before any processing, so that they don't affect the signal estimates. In this regard, some example embodiments may incorporate principles and techniques aimed at computing the signal to noise ratio (SNR) for each region of the face. Some embodiments do so by throwing away a region if its SNR is below a threshold SNR or if its maximum amplitude is above a threshold amplitude. Therefore, only a select few facial regions may be chosen for further processing, thereby reducing the complexity of signal estimation.

Referring to FIG. 1A, the iPPG system 100 jointly analyzes the plurality of spatial regions 103 in order to estimate the vital sign to reduce the effect of noise. According to some example embodiments, the vital sign may be one or a combination of pulse rate of the subject, and a heart rate variability (also referred to as "heartbeat signal") of the subject. In some embodiments, the vital sign of the subject may be a one-dimensional signal, where the dimension is a time dimension.

Some embodiments are based on the understanding that the vital sign may be estimated accurately by adopting temporal analysis. As such, the iPPG system 100 is configured to extract multidimensional time series data 108 from the sequence of images corresponding to different regions of the skin of the subject, where the multidimensional time series data 108 is used to determine the PPG signal to accurately estimate the vital sign. Some embodiments are also based on the revelation that when RGB cameras are used to acquire the video 105, in order to improve the sensitivity to illumination variations, the iPPG system 100 is configured to compute one or more ratios of the one of the color channels to another color channel in the video 105.

The estimated multidimensional time series data 108 is provided to the PPG estimator module 109 to recover a signal of interest (PPG signal) from the noisy multidimensional time-series data 108. The PPG estimator module comprises a cross-domain unrolling algorithm 109*a* configured to recover and output the PPG signal. The cross-domain unrolled iPPG algorithm 109*a* is implemented by unrolling the iterations of a model-based proximal descent algorithm for the PPG estimator module 109. Each iteration contains a gradient computation step 109*b* that reduces a data-fitting error term and one or more denoisers 109*c* that help bring the output of the gradient step closer to a clean PPG signal. Using the recovered PPG signals after a certain number of iterations of the cross-domain unrolled iPPG algorithm 109*a*, some vital signs 111 of the subject may be estimated. For example, the estimate of a vital sign in the time window may be considered as the frequency component for which the power of the frequency spectrum is maximum.

The number of iterations of the algorithm 109*a* may be a dynamic variable defined by an operator or may be defined in relation to the vital sign being estimated. In some example embodiments, an input from an operator may be provided to run the algorithm 109*a* for the defined number of iterations. In some other example embodiments, the threshold for the number of iterations may be fetched from a database defining the number of iterations in relation to one or more of the vital sign to be estimated, the body part considered for imaging, gender, age, or other physiological properties of the subject. In some example embodiments, the threshold for the number of iterations may be a hyperparameter of the iPPG algorithm 109*a*. The value corresponding to the number of iterations may serve as a termination condition for the algorithm 109*a*.

It should be noted that in some cases, the cross-domain unrolling algorithm 109*a* estimates the iPPG signal in frequency domain. The noise in the timeseries data 108 is processed by the algorithm 109*a* in frequency domain. Doing this constrains the timeseries data 108 to be restricted to only few frequencies. Also, in some example embodiments, the timeseries data which is in time domain may be transformed into frequency domain prior to determining the difference between the output signal and its ground truth.

Figure 1B:
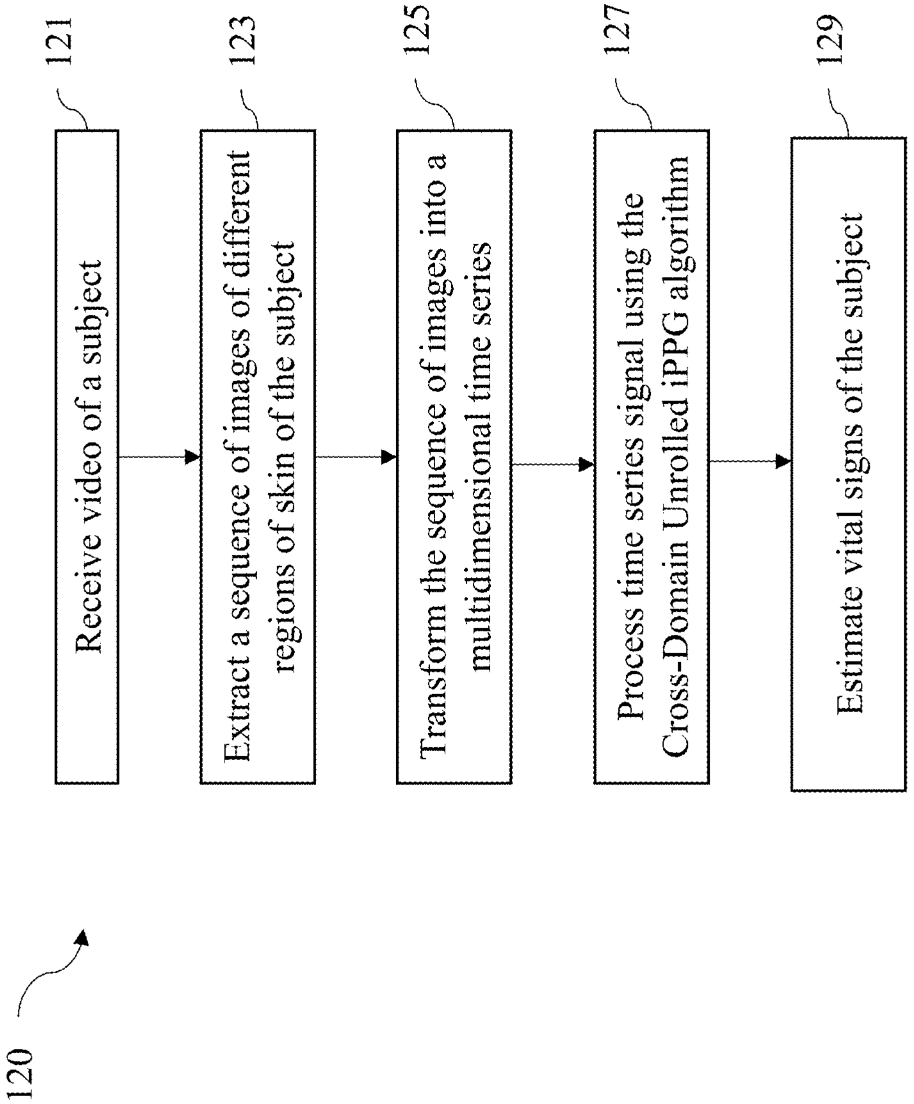
FIG. 1B illustrates a flowchart of a method executed by the iPPG system for estimating a vital sign of a subject, according to some example embodiments.

FIG. 1B illustrates a flowchart of a method 120 executed by the iPPG system 100 for estimating a vital sign 111 of a subject, according to some example embodiments. FIG. 1B is described in conjunction with FIG. 1A. The video 105 of the subject is received 121 by the iPPG system 100. The video 105 may be live video of the subject or a pre-recorded video and may correspond to at least one body part (for example the face) of the subject. The video 105 is captured under a suitable illumination spectrum such as in the NIR or visible or a broad spectrum visible and NIR wavelengths.

The iPPG system 100 extracts 123 a sequence of images of different regions of the skin of the subject. To that end, the iPPG system 100, for each video 105, obtains an image (for example, image 107) from each image frame of the video 105. Each image is partitioned or segmented into a plurality of spatial regions (for example, the spatial regions 103) resulting into a sequence of images corresponding to different areas of the body part (for example, the face). The partitioning of the image 107 is performed such that each spatial region comprises a specific area, of the body part, that is strongly indicative of the PPG signal. Thus, each spatial region of the plurality of spatial regions 103 is a region of interest (ROI) for determining PPG signal.

For each of the spatial region a time-series signal is derived using the time-series extraction module 101. As such, the time-series extraction module 101 of the iPPG system 100 transforms 125 the sequence of images into multidimensional timeseries data 108. In some example embodiments, for each video 105, the time-series extraction module 101 may extract a 5-dimensional time series data corresponding to pixel intensities over time of 5 facial regions (ROI), where the facial regions correspond to the plurality of spatial regions 103. In some embodiments, the multidimensional time series signal may have more or less than 5 dimensions corresponding to more or less than 5 facial regions. In some embodiments, the 5 facial regions may correspond to the right cheek, left cheek, chin, right forehead and the left forehead. The time-series extraction module 101 is configured to transform 125 the sequence of images corresponding to the plurality of spatial regions 103 into the multidimensional time-series signal. To that end, pixel-intensity variations of pixels from each spatial region of the plurality of spatial regions (also referred to as "different spatial regions") 103 at an instance of time may be averaged to produce values of different dimensions of the multidimensional time-series signal for the instance of time.

In some embodiments, the time-series extraction module 101 may be further configured to temporally window (or segment) the multidimensional time series signals. Accordingly, there may be a plurality of segments of the multidimensional time series signals, where at least some part of each segment of the plurality of segments overlaps with a subsequent segment of the plurality of segments forming a sequence of overlapping segments. Further, each of the segment may be normalized before submitting the multidimensional time series signals to the PPG estimator module 109. The windowed sequences may be of specific durations with a specific frame stride at interference (e.g., 10 seconds duration (250 frames at 25 fps) with a 10-frame stride at the inference), where stride indicates number of frames (e.g., 10-frames) shift over the windowed sequence (e.g., the 10 seconds windowed sequences).

Figure 1C:
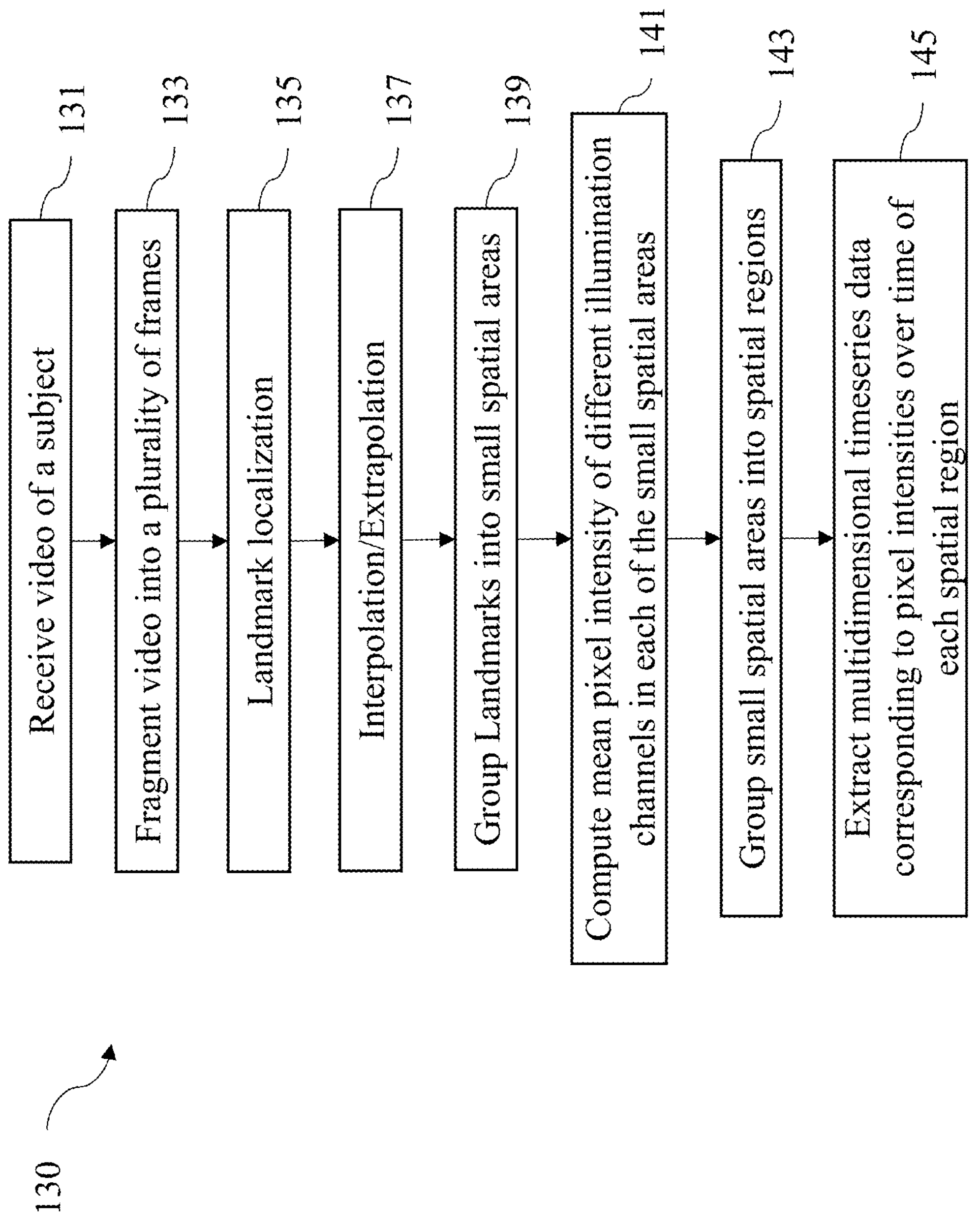
FIG. 1C illustrates a flowchart of a method for extracting multi-dimensional timeseries data from a video of the subject, according to some example embodiments.

Referring back to FIG. 1A, the time-series extraction module 101 is configured to receive a plurality of frames of the video 105 and to extract the multidimensional time series 108 from the plurality of frames. FIG. 1C illustrates a flowchart of a method for extracting multi-dimensional timeseries data from a video of the subject, according to some example embodiments. The captured video 105 of the subject is received 131 by the time series extraction module 101 of the iPPG system 100 and is fragmented 133 into a plurality of frames. The individual frames of the video 105 may correspond to an image 107 of at least one body part of the subject and as such the frames of the video 105 may yield a sequence of images. The sequence of images may correspond to different regions of a skin of the subject, where each region in the sequence includes pixels of different intensities indicative of variation of coloration of the skin. In the image 107 of FIG. 1A skin regions that are located on the face (facial regions) are shown, however it may be contemplated that various embodiments are not limited to using the face. In some embodiments, the sequence of images corresponding to other regions of exposed skin, such as the person's neck or wrists may be obtained and processed by the time-series extraction module 101.

The time series extraction module 101 detects frames having a desired body part of the subject and selects those frames for further processing. For example, the time series extraction module 101 may detect for the face of the subject in each RGB video frame. Next landmark localization 135 is used and interpolation/extrapolation 137 of its 68-landmark output to 145 landmarks is performed. That is, to extract the ROI associated with a specific body part of the subject in the image 107 of FIG. 1A, a plurality of landmarks locations corresponding to the specific body part of the subject is localized 135 in each image frame of the video 105. Therefore, the plurality of landmark locations may vary depending on the body part used for PPG signal determination. In an example embodiment, when the face of the person is used for determining the PPG signal, 68 landmark locations corresponding to the face of the person (i.e., 68 facial landmarks) are localized in each image frame of the video 105.

Some embodiments are based on the realization that image averaging reduces the impact of quantization noise of a camera generating the video 105, motion jitter due to imperfect landmark localization, and minor deformations due to head and face motion of the person. In response to the image averaging, the plurality of landmark locations is smoothed to extract the ROIs (e.g., the 5 facial regions).

Therefore, in some embodiments, before extracting the ROI from the plurality of landmark locations, the plurality of landmark locations is smoothed using a smoothing technique such as a moving average technique. In particular, a kernel of a predetermined size is moved over the plurality of landmark locations in the image to replace pixel values, in each landmark location, operated by the kernel, by an average value of the pixel values operated by the kernel.

For instance, 68 landmark locations are smoothed using the moving average with a kernel of size 3-frames. The smoothed landmark locations are then used to extract the 5 ROI located around the forehead, cheeks, and chin. Thus, in each frame of the video 105, the average intensity of the pixels in each spatial region of the 5 spatial regions is computed. In this way, the plurality of spatial regions 103 (or ROIs) is extracted from each image, where the plurality of spatial regions 103 forms a sequence of images.

Referring back to FIG. 1C, these landmarks are grouped 139 into small spatial areas, in each of which the mean pixel intensity of each illumination channel is computed 141. For example, in some embodiments when an RGB camera is used to acquire video 105, the time series extraction module 101 is configured to compute the mean pixel intensity of the Red and Green channels. In some example embodiments, instead of using multiple illumination channels, the ratio of two illumination channels may be used as a metric for further processing. For example, one or more ratios of the one of the color channel to another color channel in the video 105 may be computed, before forming the time series 108. In the exemplar scenario where the video 105 is captured by an RGB camera, the ratio of the Red and Green channels may be used for further processing.

Thereafter, grouping 143 of the small spatial areas into spatial regions is performed based on the median intensity value of the areas within each spatial region of a defined cluster size. The multidimensional time series data is then extracted 145 corresponding to the pixel intensities over time for each spatial region. For example, the small spatial areas may be grouped into K=5 facial regions, taking the median intensity value of the areas within each facial region. This yields a 5-dimensional time series 108 for each video. In some embodiments, a Butterworth filter with cutoff frequencies [0.7, 2.5] Hz may be applied on the time series 108 so as to capture frequencies in a typical range of heart rates.

Each dimension of the multidimensional time series data 108 may correspond to a different spatial region from the plurality of spatial regions of skin of the subject in the image 107. Further, each dimension may be a signal from an explicitly tracked region of interest (ROI) of the plurality of spatial regions of the skin of the subject. The tracking reduces an amount of motion-related noise. However, the multidimensional time series data 108 may still contain significant noise due to factors such as landmark localization errors, lighting variations, 3D head rotations, and deformations such as facial expressions.

Although the estimated multidimensional time series data 108 comprises signal components reflective of the underlying pulse signal useful for the vital sign estimation, the multidimensional time series data 108 may often be noisy. Thus, the multidimensional time series data 108 may be considered as a group of measured imaging PPG signals (measured iPPG signals). As such, it is an objective of the PPG estimator to recover the noise free iPPG signals from the measured iPPG signals that are truly reflective of the underlying pulse signal useful for vital sign estimation. As such, the noise-free iPPG signals may be referred to as recovered iPPG signals.

Referring back to FIG. 1B, the PPG estimator module 109 of the iPPG system 100 processes 127 the time series data 108 using the cross-domain unrolled iPPG algorithm 109*a*, where the PPG estimator module 109 may process, with the gradient step 109*b* and the denoisers 109*c*, each segment from the sequence of overlapping of the multidimensional time series data 108. As a part of the processing 127 by the PPG estimator module 109, the cross-domain unrolling optimization iteratively minimizes a difference between the received/estimated iPPG signals and the reconstructed iPPG signals, followed by processing the reconstructed iPPG signals with an iPPG neural network trained in the frequency domain with machine learning to enforce a learned structure on the frequency coefficients of the reconstructed iPPG signals. The reconstructed iPPG signals have frequency coefficients determined in a frequency domain that are transformed into the time domain of the received iPPG signals as a part of step 127.

Having obtained the frequency coefficients, the iPPG system 100 estimates 129 the vital signs of the subject from the frequency coefficients of the reconstructed iPPG signals using any suitable technique, upon reaching a termination condition of the cross-domain unrolling optimization algorithm 109*a*.

To recover a signal of interest (recovered iPPG signal) from the noisy multidimensional time-series 108, the multidimensional time-series signal denoted by Z in FIG. 1A, is given to the PPG estimator module 109. The PPG estimator module 109 is configured to recover and output the PPG signal from the noisy multidimensional time series signal using the cross-domain unrolled iPPG algorithm 109*a*. Further, using the recovered PPG signal, some vital signs of the person may be estimated.

The Cross-Domain Unrolled iPPG algorithm 109*a* of FIG. 1A is implemented by unrolling the iterations of a model-based proximal descent algorithm for the PPG estimator module 109. Each iteration contains a gradient computation step 109*b* that reduces a data-fitting error term and one or more denoisers 109*c* that help bring the output of the gradient step closer to clean PPG signal.

For each input time window containing S frames, the time series containing the average intensity of each of K face regions in every frame is extracted. Stacking these signals into a matrix Z of size S×K, it is assumed that that these region-specific signals share a quasi-periodic pulse signal that admits a structured representation in the Fourier domain. Therefore, the observation of the heartbeat signal is modeled as $$Z = Y + E = F^{-1}X + E, \tag{1}$$

where $F^{-1}$ is the oversampled inverse Fourier Transform matrix of size S×N, Y of size S×K and X of size N×K represent the pulsatile signal in all K regions in the time domain and the frequency domain, respectively, and E is a real matrix of S×K that represents the structured noise component that captures the non-pulse-related fluctuations in the iPPG signals Z. Here, Z is measured in the time domain, and processed in the Fourier domain using the Fourier transform F. This is based on the realization that the Fourier domain acts as a structure enforcer on the estimated PPG signal Y in the Fourier domain where X, which is given Fourier transform on Y has a simpler structure than in the measurement domain. X is the signal processed in the Cross-Domain Unrolled iPPG algorithm 109*a*, instead of Y. On the other hand, the structured noise component E is processed by the Cross-Domain Unrolled iPPG algorithm 109*a* in the time domain. That is, X and E, which are the components of Z are processed in different domains. In this example embodiment, these two domains are Fourier domain and time domain respectively. In other embodiments, these domains can also be the wavelet domain or an appropriate dictionary learned from data.

The decomposition of Z into the signal component in the Fourier domain X and the structured noise component E have to approximately satisfy the data fidelity term:

$$D = \frac{1}{2}\left\| Z - A\begin{bmatrix} X \\ E \end{bmatrix} \right\|_F^2, \tag{2}$$

where $$A = \lfloor F^{-1} \quad I \rfloor$$

However, satisfying the data fidelity term alone for the decomposition is not sufficient as multiple combinations of X and E can be used to form Z. That is, not all decompositions return X and E with appropriate structure. Towards this end, deep denoisers are trained to discover the appropriate structure in the Fourier domain. Instead of using explicit priors such as $l_{2,1}$ regularization, the signal and noise priors are encoded implicitly as a penalty function ρ(•,•) and its learnable scores are employed as deep denoisers for X and E, respectively.

$$\min_{X,E} \frac{1}{2}\left\| Z - A\begin{bmatrix} X \\ E \end{bmatrix} \right\|_F^2 + \lambda \cdot \rho(X, E) \tag{3}$$

where $A=[F^{-1}\ I]$. The Cross-Domain Unrolled iPPG unrolls proximal gradient descent for Eq. (3) for T iterations. In each iteration, gradient updates are performed on X and E followed by forward propagation through the signal denoiser R and the denoiser for the structured noise component Q. Given a step size a, the updates on X and E are given by $$\begin{bmatrix} \tilde{X}_{t+1} \\ \tilde{E}_{t+1} \end{bmatrix} = \begin{bmatrix} X_t \\ E_t \end{bmatrix} - \alpha \nabla_{\begin{bmatrix} X \\ E \end{bmatrix}} D\left(\begin{bmatrix} X_t \\ E_t \end{bmatrix}\right), \tag{4}$$

$$X_{t+1} = R(\tilde{X}_{t+1}),$$

$$E_{t+1} = Q(\tilde{E}_{t+1}).$$

where $X_{t+1}$ corresponds to the update on $X_t$ and $E_{t+1}$ corresponds to the update on $E_t$. In some embodiments, to find the heart rate, power in every frequency bin across all K regions are summed, and the frequency with the maximum power is selected to b the frequency of the signal representing the heart rate. For example, in one embodiment an estimated vital sign is the frequency of the heartbeat of the subject over the period of time.

In the proposed Unrolled iPPG architecture of the iPPG system 100, one or more encoder-decoder denoiser architecture is applied to the output of the gradient step 109*b* in each iteration. Thus, the PPG estimator module 109 comprises one or more time-series denoiser neural networks (also referred to as "denoisers") 109*c*. The gradient step 109*b* and the denoisers 109*c* are performed successively for T iterations to process the multidimensional time-series data to accurately determine the PPG waveform in the Cross-Domain Unrolled iPPG system 109*a*, where the PPG waveform are used to estimate the vital sign of the person. The number of iterations T may be considered as a hyperparameter of the iPPG algorithm 109*a*. According to some example embodiments, without limitation, for RMSE and PTE6, T=3 may give the desired performance.

In some example scenarios, the vital sign to be estimated for the subject may be a heartbeat signal while the heartbeat signal is locally periodic and where a period of heart rate may change over time. In such a case, some embodiments are based on realization that the 10 seconds window is a good compromise duration for extracting a current heart rate. The length of the stride frames may also be varied depending on the vital sign of the subject to be estimated.

Figure 2:
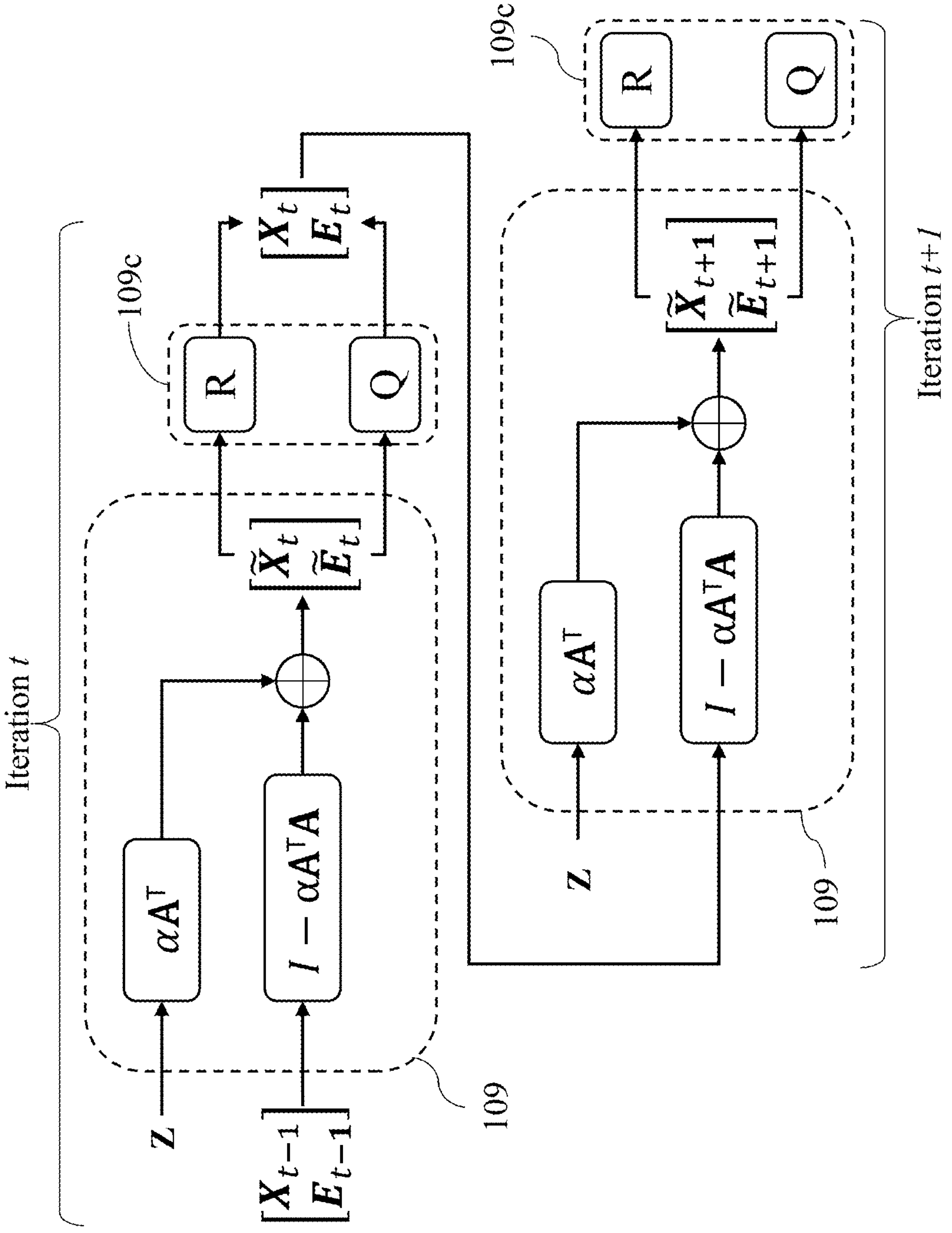
FIG. 2 illustrates two generic iterations of the cross-domain unrolled iPPG algorithm of FIG. 1A, according to some example embodiments.

FIG. 2 shows two generic iterations (iteration/and iteration t+1) of the Cross-Domain Unrolled iPPG algorithm 109*a* that is implemented in the PPG estimator module 109. The multidimensional time series 108 (e.g., 5 dimensions of the time sequence) is fed into the PPG estimator module 109 as channels. The PPG estimator module 109 comprises the Cross-Domain Unrolled iPPG algorithm implemented as a sequence of unrolled iterations of a proximal gradient descent algorithm. Each iteration consists of a gradient step 109*b* and the proximal operators are replaced by trainable cross-domain denoisers 109*c* R and Q. The channels corresponding to the multidimensional time-series signal are combined during the gradient step and during the forward pass in the sequence of layers in the denoisers 109*c*. In the PPG estimator module 109, T iterations of the gradient steps 109*b* and denoisers 109*c* map the multidimensional time series signal to the desired PPG signal. For each windowed sequence of the multidimensional time-series signal (e.g., the 10-second window), the Cross-Domain Unrolled iPPG architecture 109*a* extracts the PPG signal from the multidimensional time series 108 obtained from the ROIs.

Figure 3:
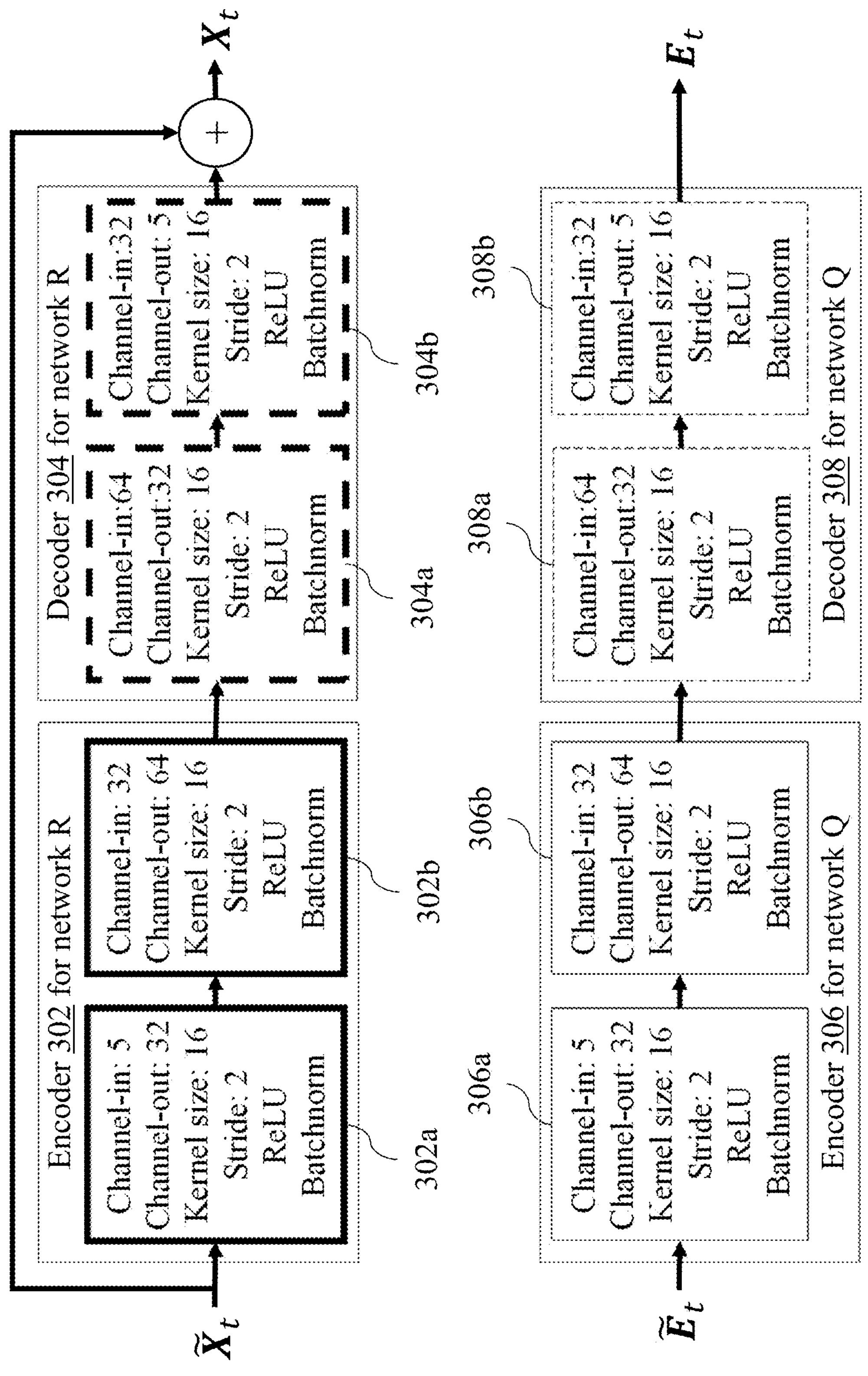
FIG. 3 illustrates an architecture of denoisers utilized by the iPPG system of FIG. 1A, according to some example embodiments.

FIG. 3 illustrates an architecture of denoisers Rand Q utilized by the iPPG system of FIG. 1A, according to some example embodiments. In cross-domain unrolled iPPG, the learned neural network denoisers R and Q are modeled using an encoder-decoder architecture. As is shown in FIG. 3, the encoder 302 for the network R is realised through the blocks 302*a* and 302*b*, the decoder for the network R is realised through the blocks 304*a* and 304*b*, while the encoder for the network Q is realised through the blocks 306*a* and 306*b* and the decoder for the network Q is realised through the blocks 308*a* and 308*b*. As the network R operates on Fourier coefficients $X_t$, its network weights are complex-valued (blocks shown in bold thick bounds), while the network weights for Q which operates on $E_t$, are real-valued (blocks shown in thin bounds). The networks consist of two downsampling convolutional blocks 302*a* and 302*b* for network R and 306*a* and 306*b* for network Q, with a stride of 2, in which the number of channels is increased from 5 to 32 and then from 32 to 64. The two upsampling blocks 304*a* and 304*b* for network R and 308*a* and 308*b* for network Q, are implemented using transposed convolution with a stride of 2, decreasing the number of channels from 64 to 32 and from 32 to 5. Each convolutional layer has a kernel size of 16 in the temporal dimension and is followed by a ReLU nonlinearity and then a batch normalization layer.

In some embodiments, during training, parameters of the neural networks R and Q are updated so as to minimize the mean squared error loss between the output signal after T unrolled iterations, $Y^T=F^{-1}X^T$, and the ground-truth waveform $Z_{gt}$. Minibatch stochastic gradient descent using backpropagation may be used to update the parameters of the denoisers Rand Q.

The specifics of some training dataset used for the denoisers and experimental details related to the performance of the cross domain unrolled iPPG algorithm are described next. In some example embodiments, the cross-domain unrolled iPPG algorithm 109*a*, may be trained using the Multimodal Spontaneous Expression-Heart Rate (MMSE-HR) dataset. This dataset contains 102 videos, from 23 female subjects and 17 male subjects, capturing the face and simultaneous blood pressure wave from a finger sensor as various emotions are elicited. This results in substantial motion in some videos, to which Cross-Domain Unrolled iPPG algorithm is robust. Videos were captured at a resolution of 1040×1392 at 25 frames per second, while the blood pressure wave was measured at 1000 samples per second. The ground-truth data are downsampled to match the frame rate of the videos in the experiments ializing the convolution layers to output 0 and adding a single skip connection at the highest convolution layer. The variable X, which is input to R, is initialized as the Fourier transform of Z. The noise E, which is input to Q, is initialized as the 0 matrix. The mean squared error between each of the five output channels and the ground-truth is calculated, and the gradients are used to update the parameters of the denoisers R and Q using the Adam optimizer with a learning rate of $3\times10^{-4}$ for 8 epochs. To be able to estimate heart rates at the lower and higher end that are not well represented in the dataset, training data are augmented using augmentations called "SpeedUp" and "SlowDown". For the "SlowDown" augmentation, an input window of length S is cropped by a random percentage between 20% and 40%, and interpolated back to the original window size S using linear interpolation. For the "SpeedUp" augmentation, given the window length S, an input window length is randomly chosen that is 20% to 40% larger than the target time windows (e.g. 1.2×S), and linearly interpolate it back to length S.

During training, each empirical and ground-truth waveform are partitioned into 10-second windows, then shift the window by 2.4 seconds to get the next partially overlapping window for training. The windows are loaded randomly during training with a batch size of 100. At test time, 10-second segments are reconstructed in a nonoverlapping fashion.

For evaluation, the mean absolute error (MAE) and root mean squared error (RMSE) of the ground-truth and predicted heart rate computed for 30-second time windows for the test videos are reported. To this end, three adjacent 10-second output windows from the Unrolled iPPG system are concatenated in order to perform evaluation on 30-second windows. The MAE and RMSE metrics are averaged over all B windows for all test videos and over all test set partitions. A metric called PTE6, the percent of time the heart rate error is less than 6 beats per minute (bpm), which is a way to measure how often the estimated heart rate is correct, is also reported.

FIG. 4 illustrates a tabular comparison of performance of the unrolled iPPG system of FIG. 1A with that of some known methods. Unrolled iPPG significantly outperforms model-based methods such as AutoSparsePPG by reducing the MAE error from 4.55 bpm to 1.26 bpm, and the RMSE from 14.42 bpm to 3.87 bpm. PTE6 also increases from 88.10% to 94.57%. Given that Unrolled iPPG incorporates learned components, it is also compared with data-driven methods CAN and InverseCAN. Unrolled iPPG outperforms both CAN and InverseCAN. Compared to InverseCAN, our Unrolled iPPG method reduces the MAE from 2.27 bpm to 1.26 bpm and the RMSE from 4.90 bpm to 3.87 bpm.

Figure 5A:
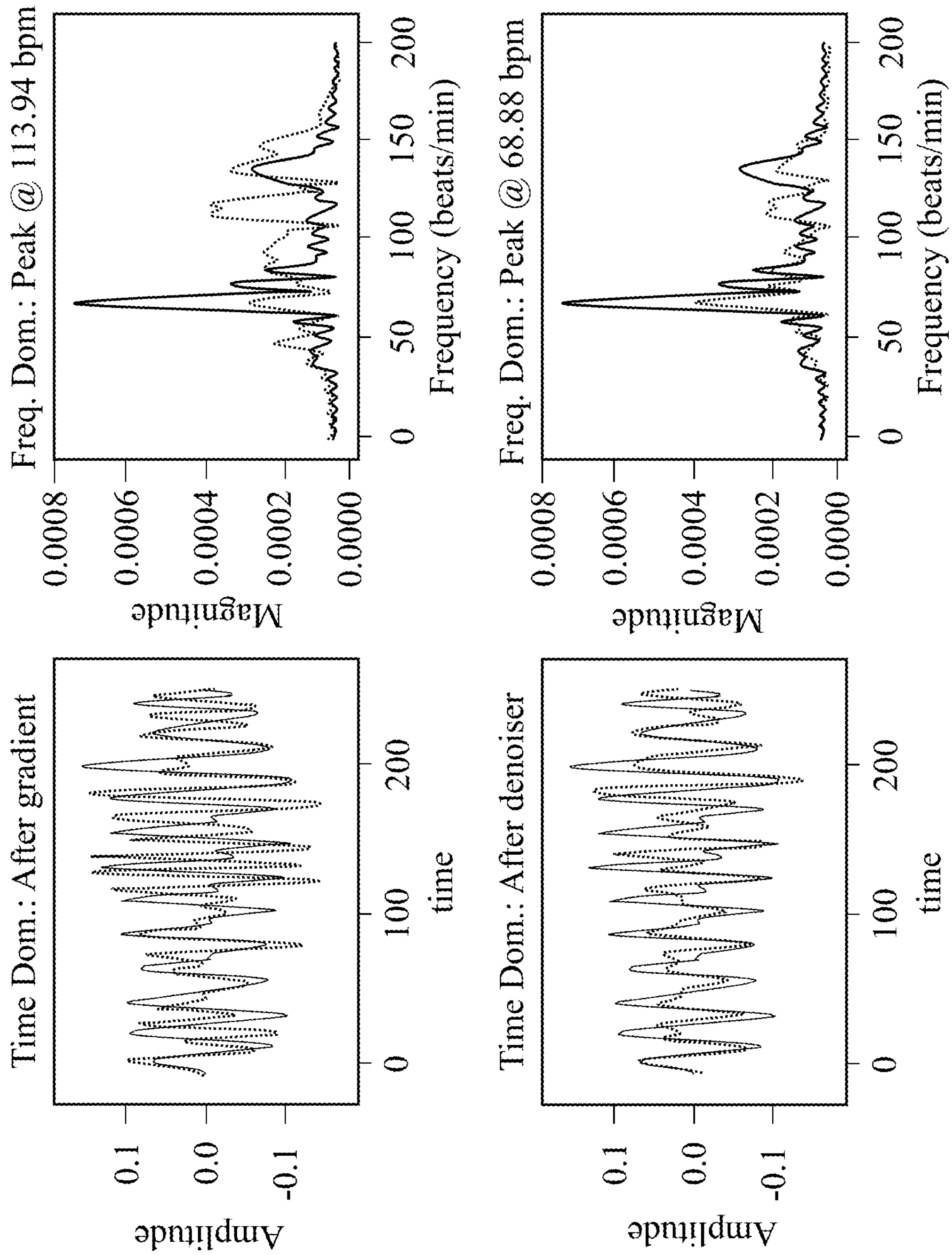
FIGS. 5A-5C show exemplar iterations of the unrolled iPPG algorithm for estimating the underlying pulse signal and spectrum for one test video in MMSE-HR dataset, according to some example embodiments.
Figure 5B:
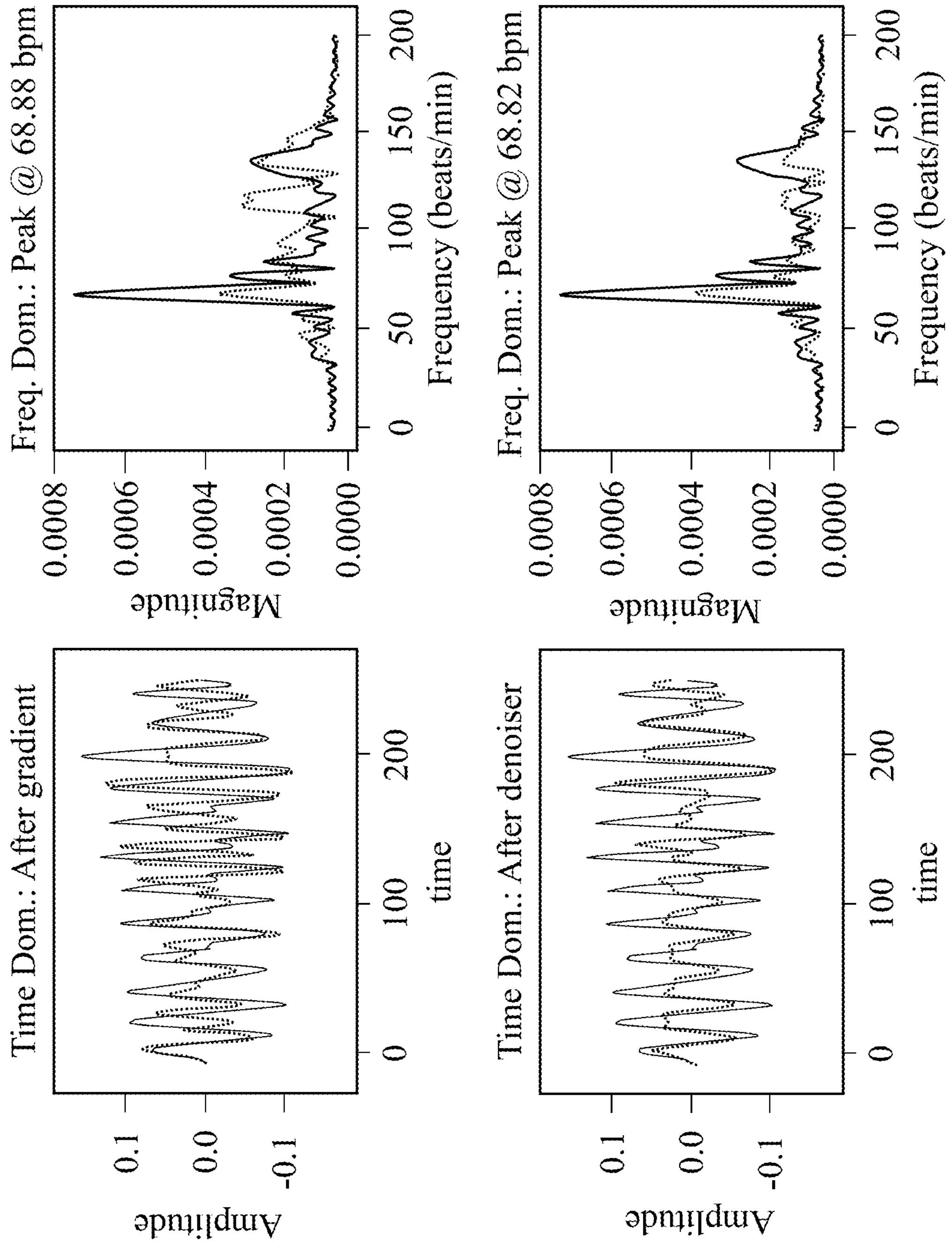
Figure 5C:
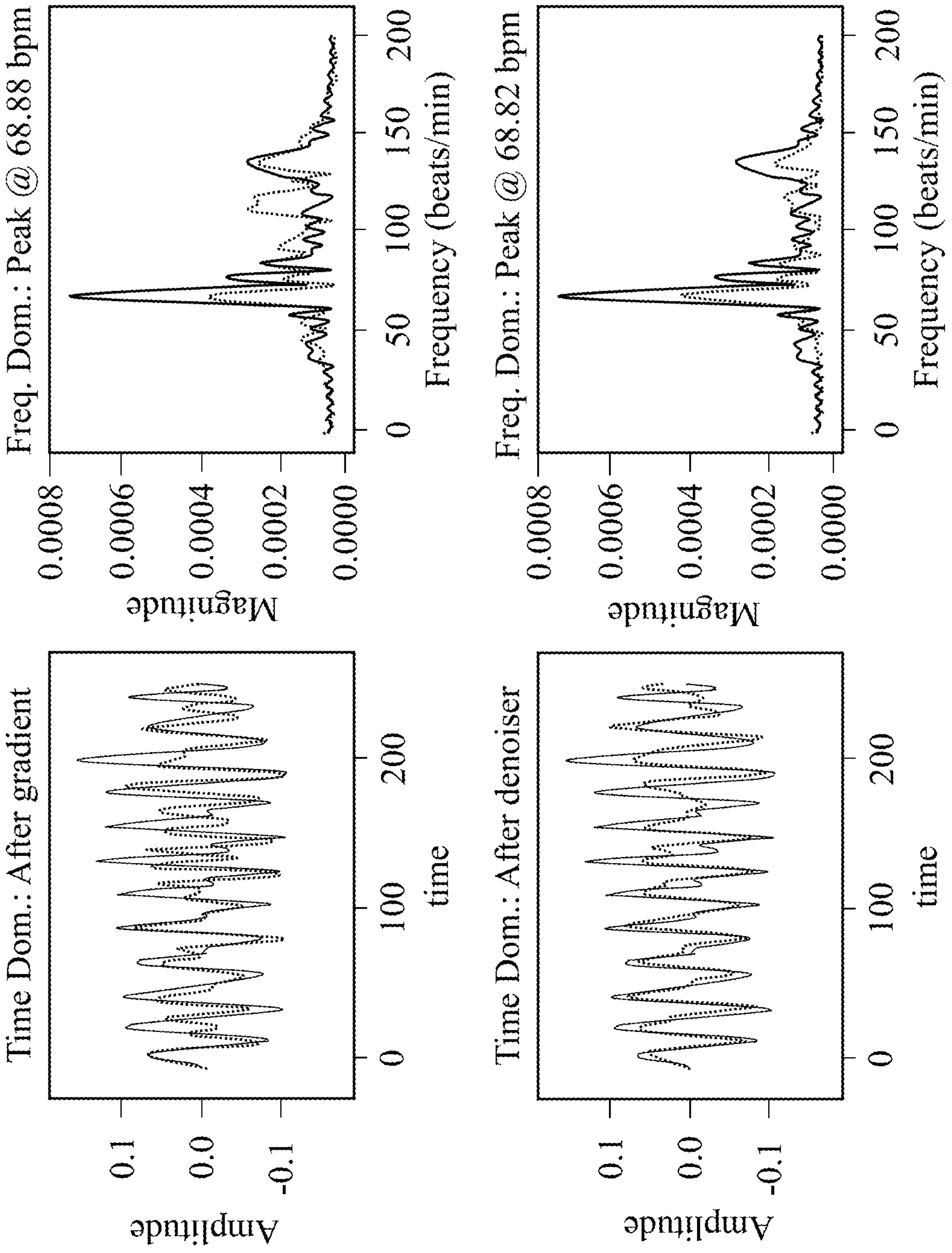

FIGS. 5A-5C show an example of how Unrolled iPPG iteratively estimates the underlying pulse signal and spectrum for one test video in MMSE-HR dataset. Particularly, FIG. 5A illustrates a first iteration of the Unrolled iPPG estimation, FIG. 5B illustrates a subsequent second iteration of the Unrolled iPPG estimation, and FIG. 5C illustrates a subsequent third iteration of the Unrolled iPPG estimation. In each of the FIGS. 5A-5C, the projected curve is shown as dotted while the ground truth curve is shown as solid. Comparing the outputs of the first, second and third iterations to the true signal, the reconstructed iPPG signals gets progressively closer to the true signal as the iterations progress.

Figure 5D:
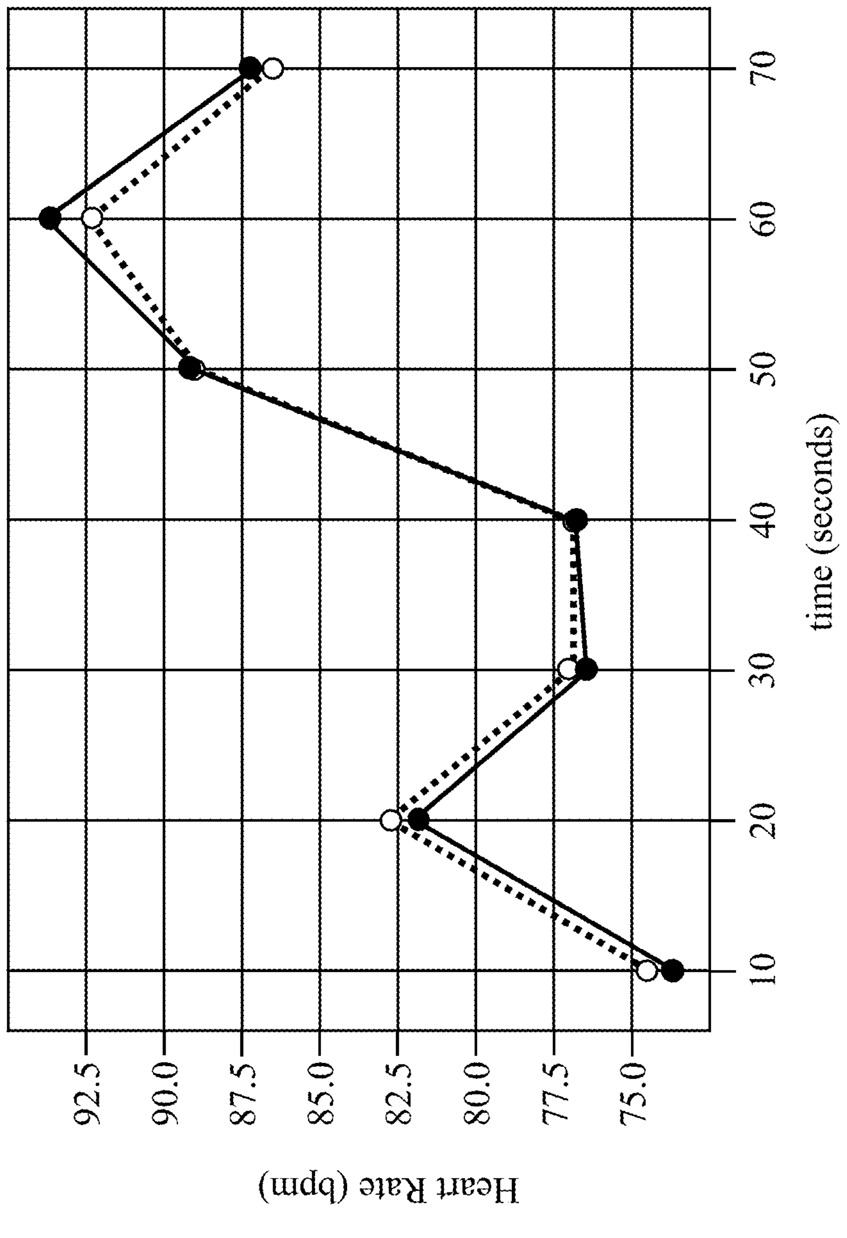
FIG. 5D shows the heart rate estimation performance of the Unrolled iPPG system for 10-second consecutive windows in a test video, according to some example embodiments.

FIG. 5D shows an example of Unrolled iPPG performance (shown as dashed line as the estimated heart rate in bpm) on consecutive 10-second time window for test video in MMSE-HR dataset. Unrolled iPPG system (dashed curve) correctly predicts the ground-truth heart rate (shown as solid curve) over a wide range of heart rates and across the duration (along horizontal axis in seconds) of an entire video.

In FIG. 6, the effect of modeling the noise explicitly using a denoiser Q (instead of modeling the Fourier coefficients and noise simultaneously in R) on heart rate estimation performance is shown. Using both Q and R significantly improves the results, compared to having just R. The network Q learns the structure of the noise, which can be subtracted from the signal Z in Eq. (1) to obtain the underlying pulse signal.

In FIG. 7, an example scenario showing the effect of the number of unrolling iterations T (the successive gradient and denoising steps) on the heart estimation performance is analyzed. The results show that T=3 unrolled iterations provide the best performance.

Figure 8:
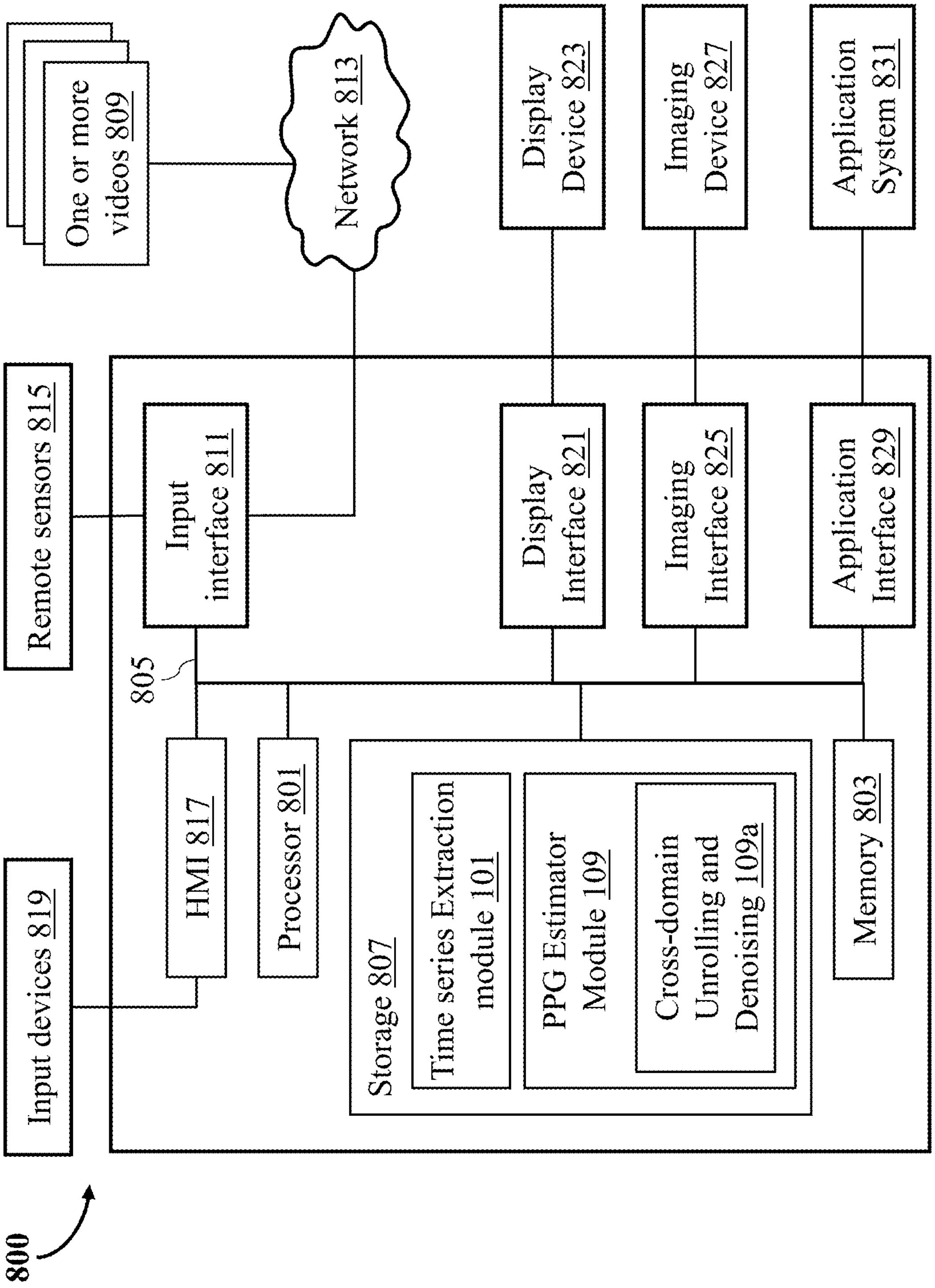
FIG. 8 illustrates a block diagram of a computing system for implementing some components of an unrolled iPPG system, according to some example embodiments.

FIG. 8 illustrates a block diagram of an iPPG system 800, according to an example embodiment. The system 800 includes a processor 801 configured to execute stored instructions, as well as a memory 803 that stores instructions that are executable by the processor 801. The processor 801 may be a single core processor, a multi-core processor, a computing cluster, or any number of other configurations. The memory 803 can include random access memory (RAM), read only memory (ROM), flash memory, or any other suitable memory systems. The processor 801 is connected through a bus 805 to one or more input and output devices.

The instructions stored in the memory 803 correspond to an iPPG method for estimating the vital signs of the person based on a set of iPPG signals' waveforms measured from different regions of a skin of a subject. The iPPG system 800 may also include a storage device 807 configured to store various modules such as the time-series extraction module 101 and the PPG estimator module 109, where the PPG estimator module 109 comprises the implemented Cross-Domain Unrolled iPPG algorithm 109*a*. The aforesaid modules stored in the storage device 807 are executed by the processor 801 to perform the vital signs estimations. The vital sign may correspond to a pulse rate of the person or heart rate variability of the person. The storage device 807 may be implemented using a hard drive, an optical drive, a thumb drive, an array of drives, or any combinations thereof.

The time-series extraction module 101 obtains an image in each frame of a video of one or more videos 809 that is fed to the iPPG system 800, where the one or more videos 809 comprises a video of a body part of a subject whose vital signs are to be estimated. The one or more videos may be recorded by one or more suitable imaging devices. The time-series extraction module 101 may partition the image from each frame into a plurality of spatial regions corresponding to ROI of the body part that are strong indicators of PPG signal, where the partitioning of the image into the plurality of spatial regions form a sequence of images of the body part. Each image comprises different region of a skin of the body part in the image. The sequence of images may be transformed into a multidimensional time-series signal in the manner described previously with reference to FIG. 1C. The multidimensional time-series signal may be provided to the PPG estimator module 109. The PPG estimator module 109 may utilize the Cross-Domain Unrolled iPPG algorithm 109*a* to process the multidimensional time-series signal by performing a series of unrolled iterations that performs a gradient step 109*b* to reduce the data fidelity error term and passed through one or more denoisers 109*c* in succession for T iterations to estimate the PPG waveform, where the PPG waveform is used to estimate the vital signs of the person.

The iPPG system 800 includes an input interface 811 such as an input port to receive the one or more videos 809. For example, the input interface 811 may be a network interface controller adapted to connect the iPPG system 800 through the bus 805 to a network 813.

Additionally or alternatively, in some implementations, the iPPG system 800 is connected to a remote sensor 815, such as an imaging sensor, to collect the one or more videos 809. In some implementations, a human machine interface (HMI) 817 within the iPPG system 800 connects the iPPG system 800 to input devices 819, such as a keyboard, a mouse, trackball, touchpad, joystick, pointing stick, stylus, touchscreen, and among others to receive inputs from a user or operator.

The iPPG system 800 may be linked through the bus 805 to an output interface to render the PPG waveform. For example, the iPPG system 800 may include a display interface 821 adapted to connect the iPPG system 800 to a display device 823, wherein the display device 823 may include, but not limited to, a computer monitor, a projector, or mobile device.

The iPPG system 800 may also include and/or be connected to an imaging interface 825 adapted to connect the iPPG system 800 to an imaging device 827.

In some embodiments, the iPPG system 800 may be connected to an application interface 829 through the bus 805 adapted to connect the iPPG system 800 to an application system 831 that can be operated based on the estimated vital signals. In an exemplary scenario, the application system 831 may be a patient monitoring system, which uses the vital signs of a patient. In another exemplary scenario, the application system 831 is a driver monitoring system, which uses the vital signs of a driver to determine if the driver can drive safely, e.g., whether the driver is drowsy or not.

Figure 9:
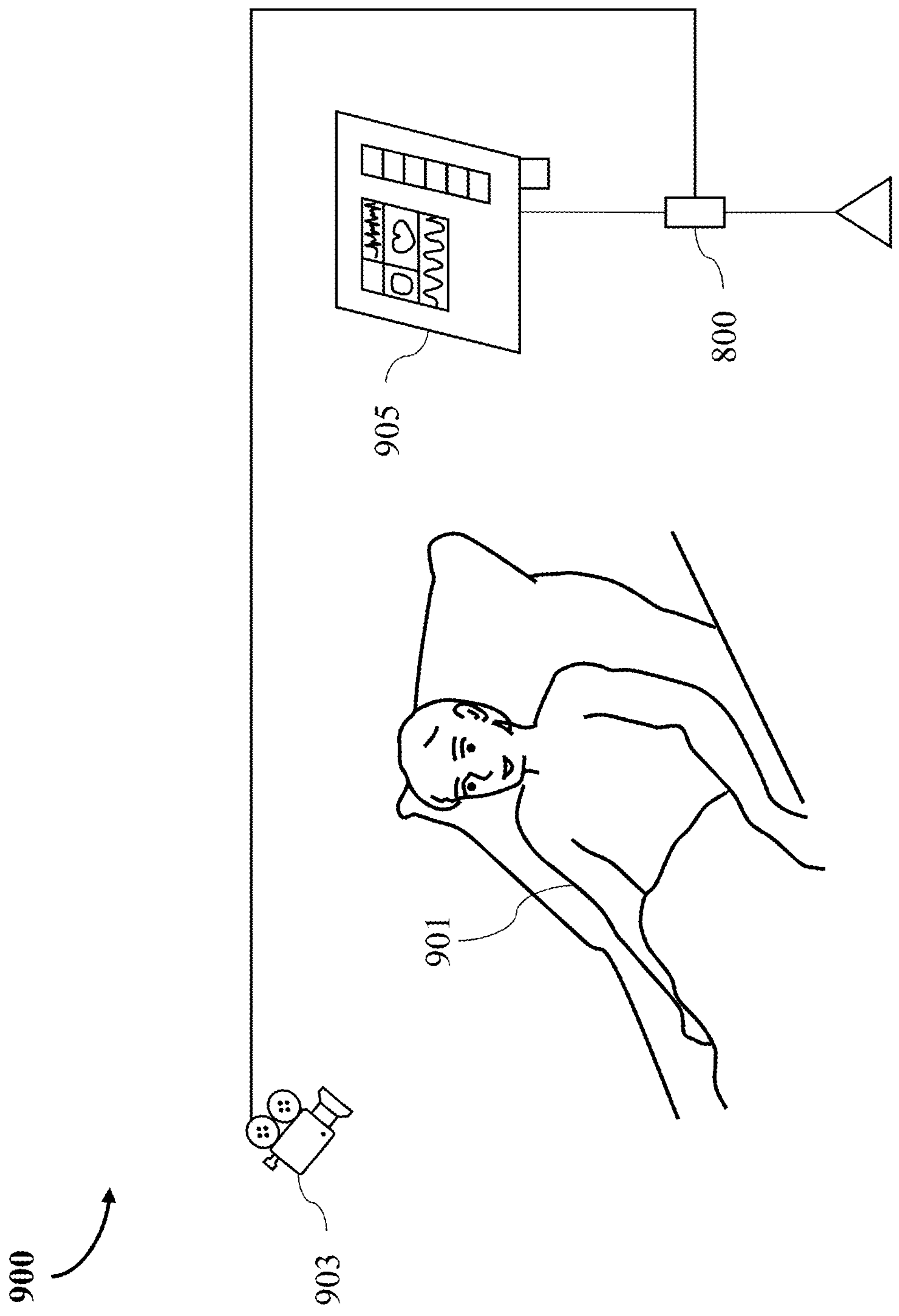
FIG. 9 illustrates a patient monitoring system using the iPPG system of FIG. 1A or FIG. 8, according to some example embodiments.
Figure 10:
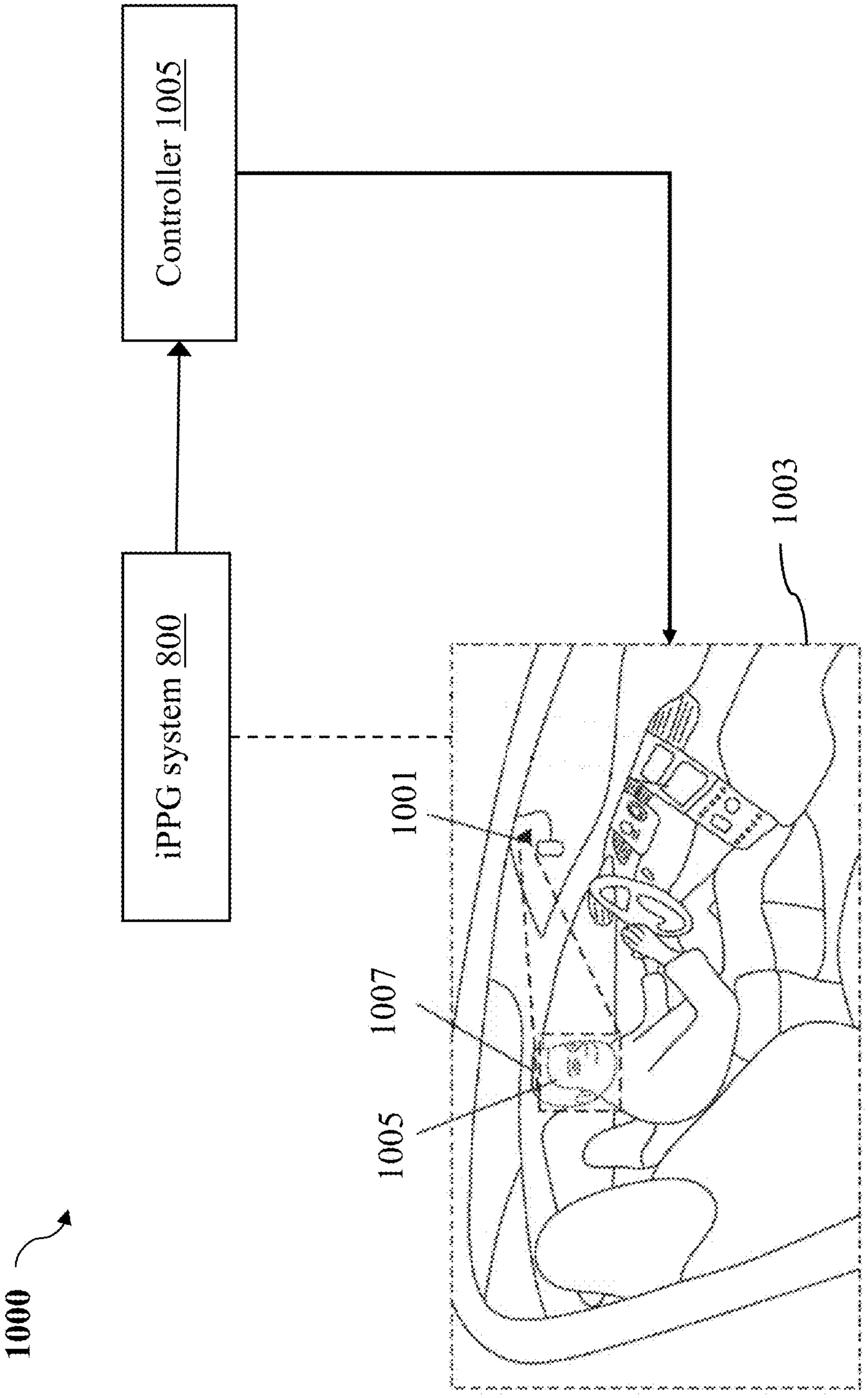
FIG. 10 illustrates a passenger assistance system using the iPPG system of FIG. 8, according to some example embodiments.

The proposed approaches for estimating vital signs of subjects may be used for several control applications, some of which are described next with reference to FIGS. 9 and 10.

In some example embodiments, the subject whose vital signs are to be estimated may be a patient. In such example scenarios, the iPPG system may be used for monitoring the vital signs of the patient. FIG. 9 illustrates an example patient monitoring system 900 using the iPPG system 100 or 800, according to an example embodiment. To monitor vital signs of the patient 901, a camera 903 is used to image the patient 901 to obtain a video sequence of the patient 901. The camera 903 may include a CCD or CMOS sensor for converting incident light and the intensity variations thereof into an electrical signal. The camera 903, particularly non-invasively, captures light reflected from a skin portion of the patient 901. A skin portion may thereby particularly refer to the forehead, neck, wrist, part of the arm, or some other portion of the patient's skin. A light source, e.g., a near-infrared light source, may be used to illuminate the patient or a region of interest including a skin portion of the patient.

Based on the captured images, the iPPG system 800 determines the vital signs of the patient 901 according to the example embodiments described previously. In particular, the iPPG system 800 determines the vital signs such as the heart rate, the breathing rate or the blood oxygenation of the patient 901. Further, the determined vital signs may be displayed on an operator interface 905 for presenting the determined vital signs. Such an operator interface 905 may be a patient bedside monitor or may also be a remote monitoring station in a dedicated room in a hospital or even in a remote location in telemedicine applications.

In some example embodiments, the subject whose vital signs are to be estimated may be a driver or a passenger in a vehicle. FIG. 10 illustrates a passenger assistance system 1000 using the iPPG system 800, according to an example embodiment. The NIR light source and/or a NIR camera 1001 are arranged within a vehicle 1003. In particular, the NIR camera 1001 may be arranged in a field of view (FOV) 1007 capturing the driver or passenger 1005. The iPPG system 800 is integrated into the vehicle 1003. The NIR light source is configured to illuminate skin of an occupant of the vehicle such as the driver or passenger 1005, and the NIR camera 1001 is configured to record the video of the driver or passenger 1005 in real time. Further, the NIR videos are fed to the iPPG system 800 to measure the iPPG signals from different regions of the skin of the driver or passenger 1005. The iPPG system 800 receives the measured iPPG signals and determines the vital sign, such as pulse rate, of the driver or passenger 1005.

Having obtained the vital sign of the passenger or driver 1005, the iPPG system 800 may process the estimated vital sign to check for a condition of the passenger or driver 1005. In some example embodiments, the processing of the estimated vital sign of the passenger or driver 1005 may be performed by a control system of the vehicle 1003 or a remote server communicatively coupled with the control system of the vehicle 1003. For example, an estimated vital sign of the passenger or driver 1005 may be compared with a permissible threshold to ascertain a medical fitness of the passenger or driver 1005. If the result of comparison indicates that the medical fitness of the passenger or driver 1005 is not suitable, an appropriate action may be initiated. For example, the processor of iPPG system 800 may produce one or more control action commands, based on the estimated vital signs of the driver 1005 of the vehicle 1003. The one or more control action commands may include vehicle braking, steering control, generation of an alert notification, initiation of an emergency service request, or switching of a driving mode from manual to automatic or vice versa. The one or more control action commands may be transmitted to the controller 1005 of the vehicle 1003. The controller 1005 may control the vehicle 1003 according to the one or more control action commands. For example, if the determined pulse rate of the driver is very low, then the driver 1005 may be experiencing a heart attack. Consequently, the iPPG system 800 may produce control commands for reducing a speed of the vehicle and/or steering control (e.g., to steer the vehicle to a shoulder of a highway and make it come to a halt) and/or initiate an emergency service request.

In this way, several example embodiments described herein may be used in real world applications for medical diagnosis and well being, vehicle assistance, and patient monitoring.

The above description provides exemplary embodiments only, and is not intended to limit the scope, applicability, or configuration of the disclosure. Rather, the above description of the exemplary embodiments will provide those skilled in the art with an enabling description for implementing one or more exemplary embodiments. Contemplated are various changes that may be made in the function and arrangement of elements without departing from the spirit and scope of the subject matter disclosed as set forth in the appended claims.

Specific details are given in the above description to provide a thorough understanding of the embodiments. However, understood by one of ordinary skill in the art can be that the embodiments may be practiced without these specific details. For example, systems, processes, and other elements in the subject matter disclosed may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed but may have additional steps not discussed or included in a figure. Furthermore, not all operations in any particularly described process may occur in all embodiments. A process may correspond to a method, a function, a procedure, a subroutine, a subprogram, etc. When a process corresponds to a function, the function's termination can correspond to a return of the function to the calling function or the main function.

Furthermore, embodiments of the subject matter disclosed may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. Typically, the functionality of the program modules may be combined or distributed as desired in various embodiments.

Embodiments of the present disclosure may be embodied as a method, of which an example has been provided. The acts performed as part of the method may be ordered in any suitable way. Accordingly, embodiments may be constructed in which acts are performed in an order different than illustrated, which may include performing some acts concurrently, even though shown as sequential acts in illustrative embodiments. Although the present disclosure has been described with reference to certain preferred embodiments, it is to be understood that various other adaptations and modifications can be made within the spirit and scope of the present disclosure. Therefore, it is the aspect of the append claims to cover all such variations and modifications as come within the true spirit and scope of the present disclosure.

What is claimed is:

1. A remote photoplethysmography (RPPG) system for estimating a vital sign signal of a subject, comprising:

memory configured to store instructions;

a processor configured to execute the instructions to cause the RPPG system to:

receive a sequence of imaging photoplethysmography (iPPG) signals measured from different regions of a skin of the subject in a time domain, wherein the iPPG signals correspond to non-contact optical measurements of the skin of the subject, and wherein the non-contact optical measurements are obtained from at least one detector disposed remotely from the subject;

obtain a reconstructed iPPG signals as an output of an iPPG neural network trained in a frequency domain with machine learning to enforce a learned structure on frequency coefficients of the reconstructed iPPG signals;

execute a cross-domain unrolling optimization iteratively minimizing a difference between the received iPPG signals and the reconstructed iPPG signals, wherein the reconstructed iPPG signals have the frequency coefficients determined in the frequency domain and transformed into the time domain of the received iPPG signals before computation of the difference between the received iPPG signals and the reconstructed iPPG signals;

determine the vital sign signal of the subject from the frequency coefficients of the reconstructed iPPG signals upon reaching a termination condition of the cross-domain unrolling optimization; and output the vital sign signal corresponding to the reconstructed iPPG signals via an output interface.

2. The RPPG system of claim 1, wherein the cross-domain unrolling optimization uses a gradient descent minimization for minimizing the difference between the received iPPG signals and the reconstructed iPPG signals.

3. The RPPG system of claim 1, wherein the cross-domain unrolling optimization uses a proximal gradient descent minimization for minimizing a difference between the received iPPG signals and the reconstructed iPPG signals.

4. The RPPG system of claim 1, wherein, for at least some iterations of the cross-domain unrolling optimization, the reconstructed iPPG signals are updated at least once in the time domain during the minimization of the difference between the received iPPG signals and the reconstructed iPPG signals and at least once in the frequency domain by the iPPG neural network.

5. The RPPG system of claim 1, further comprising a controller communicatively coupled to a machine, wherein the controller is configured to:

receive the vital sign of the subject; and generate one or more control commands for controlling the machine, based on the received vital sign of the subject.

6. The RPPG system of claim 1, wherein the cross-domain unrolling optimization estimates noise of the received iPPG signals and modifies the reconstructed iPPG signals with the estimated noise for minimizing the difference between the received iPPG signals and the reconstructed iPPG signals.

7. The RPPG system of claim 6, wherein the noise is processed with a noise neural network to enforce an implicit structure on the noise and generate a structured component of the noise.

8. The RPPG system of claim 7, wherein the received iPPG signals are estimated in the frequency domain, wherein the iPPG neural network processes the noise in the frequency domain to constrain the received iPPG signals to be limited to a set of active frequency coefficients, and wherein the received iPPG signals are transformed into the time domain before combining with the reconstructed iPPG signals in the time domain.

9. The RPPG system of claim 7, wherein the noise is estimated in the time domain, and the noise neural network processes the noise in the time domain to constrain the structure of the noise in a manner defined by the noise neural network.

10. The RPPG system of claim 7, wherein the noise neural network is trained with ground truth iPPG signals measured using contact sensing.

11. The RPPG system of claim 7, wherein the noise neural network comprises learned neural network denoisers that are modeled using an encoder-decoder architecture.

12. The RPPG system of claim 11, wherein weights of at least one of the learned neural network denoisers are complex-valued.

13. The RPPG system of claim 11, wherein weights of at least one of the learned neural network denoisers are real-valued.

14. The RPPG system of claim 11, wherein each of the learned neural network denoisers comprises:

two downsampling convolutional blocks with a stride of 2, in which number of channels is increased from 5 to 32 in a first block of the downsampling convolutional blocks and then from 32 to 64 in a second block of the downsampling convolutional blocks; and two upsampling blocks that are implemented using transposed convolution with a stride of 2, in which the number of channels is decreased from 64 to 32 in a third block of the upsampling blocks and from 32 to 5 in a fourth block of the upsampling blocks.

15. The RPPG system of claim 14, wherein each convolutional layer of the first block, the second block, the third block, and the fourth block has a kernel size of 16 in the temporal dimension and is followed by a ReLU nonlinearity and a batch normalization layer.

16. A computer-implemented method for estimating a vital sign signal of a subject, comprising:

receiving a sequence of imaging photoplethysmography (iPPG) signals measured from different regions of a skin of the subject in a time domain, wherein the iPPG signals correspond to non-contact optical measurements of the skin of the subject, and wherein the non-contact optical measurements are obtained from at least one detector disposed remotely from the subject;

obtaining a reconstructed iPPG signals as an output of an iPPG neural network trained in a frequency domain with machine learning to enforce a learned structure on frequency coefficients of the reconstructed iPPG signals;

executing a cross-domain unrolling optimization iteratively minimizing a difference between the received iPPG signals and the reconstructed iPPG signals, wherein the reconstructed iPPG signals have the frequency coefficients determined in the frequency domain and transformed into the time domain of the received iPPG signals before computation of the difference between the received iPPG signals and the reconstructed iPPG signals determining the vital sign signal of the subject from the frequency coefficients of the reconstructed iPPG signals upon reaching a termination condition of the cross-domain unrolling optimization; and outputting the vital sign signal corresponding to the reconstructed iPPG signals via an output interface.

17. The computer-implemented method of claim 16, further comprising:

estimating using the cross-domain unrolling optimization, noise of the received iPPG signals; and modifying the reconstructed iPPG signals with the estimated noise for minimizing the difference between the received iPPG signals and the reconstructed iPPG signals.

18. The computer-implemented method of claim 17, further comprising processing the noise with a noise neural network to enforce an implicit structure on the noise and generate a structured component of the noise.

19. The computer-implemented method of claim 18, wherein the received iPPG signals are estimated in the frequency domain, wherein the noise is processed by the noise neural network in the frequency domain to constrain the received iPPG signals to be limited to a set of active frequency coefficients, and wherein the received iPPG signals are transformed into the time domain before combining with the reconstructed iPPG signals in the time domain.

20. A non-transitory computer readable medium having stored thereon computer-executable instructions which when executed by a computer, cause the computer to perform a method for estimating a vital sign signal of a subject, the method comprising:

receiving a sequence of imaging photoplethysmography (iPPG) signals measured from different regions of a skin of the subject in a time domain, wherein the iPPG signals correspond to non-contact optical measurements of the skin of the subject, and wherein the non-contact optical measurements are obtained from at least one detector disposed remotely from the subject;

obtaining a reconstructed iPPG signals as an output of an iPPG neural network trained in a frequency domain with machine learning to enforce a learned structure on frequency coefficients of the reconstructed iPPG signals;

executing a cross-domain unrolling optimization iteratively minimizing a difference between the received iPPG signals and the reconstructed iPPG signals, wherein the reconstructed iPPG signals have the frequency coefficients determined in the frequency domain and transformed into the time domain of the received iPPG signals before computation of the difference between the received iPPG signals and the reconstructed iPPG signals;

determining the vital sign signal of the subject from the frequency coefficients of the reconstructed iPPG signals upon reaching a termination condition of the cross-domain unrolling optimization; and outputting the vital sign signal corresponding to the reconstructed iPPG signals via an output interface.

* * * * *